United States Patent
Kitagawa et al.

(10) Patent No.: US 11,020,511 B2
(45) Date of Patent: Jun. 1, 2021

(54) DEVICE AND PRODUCTION METHOD FOR THE SAME

(71) Applicant: Toray Industries, Inc., Tokyo (JP)

(72) Inventors: Rumiko Kitagawa, Otsu (JP); Masataka Nakamura, Otsu (JP)

(73) Assignee: TORAY INDUSTRIES, INC., Tokyo (JP)

( * ) Notice: Subject to any disclaimer, the term of this patent is extended or adjusted under 35 U.S.C. 154(b) by 42 days.

(21) Appl. No.: 16/070,664

(22) PCT Filed: Feb. 22, 2017

(86) PCT No.: PCT/JP2017/006615
§ 371 (c)(1),
(2) Date: Jul. 17, 2018

(87) PCT Pub. No.: WO2017/146102
PCT Pub. Date: Aug. 31, 2017

(65) Prior Publication Data
US 2019/0022282 A1    Jan. 24, 2019

(30) Foreign Application Priority Data
Feb. 22, 2016 (JP) .............................. JP2016-030687

(51) Int. Cl.
| | | |
|---|---|---|
| A61L 27/50 | (2006.01) | |
| A61L 15/00 | (2006.01) | |
| A61L 27/36 | (2006.01) | |
| A61L 31/04 | (2006.01) | |
| B32B 27/30 | (2006.01) | |
| A61L 33/06 | (2006.01) | |
| A61K 9/70 | (2006.01) | |
| B05D 7/24 | (2006.01) | |
| A61L 27/00 | (2006.01) | |

(52) U.S. Cl.
CPC ............... *A61L 27/50* (2013.01); *A61K 9/70* (2013.01); *A61L 15/00* (2013.01); *A61L 27/00* (2013.01); *A61L 27/3683* (2013.01); *A61L 31/04* (2013.01); *A61L 33/06* (2013.01); *B05D 7/24* (2013.01); *B32B 27/30* (2013.01)

(58) Field of Classification Search
CPC . A61K 9/70; A61L 15/00; A61L 27/50; A61L 27/00; A61L 31/04; B05D 7/24; B32B 27/30
See application file for complete search history.

(56) References Cited

U.S. PATENT DOCUMENTS

| | | |
|---|---|---|
| 4,168,112 A | 9/1979 | Ellis et al. |
| 4,321,261 A | 3/1982 | Ellis et al. |
| 8,480,227 B2 | 7/2013 | Qiu et al. |
| 9,052,442 B2 | 6/2015 | Pruitt et al. |
| 9,505,184 B2 | 11/2016 | Kolluru et al. |
| 2002/0006521 A1 | 1/2002 | Shimoyama et al. |
| 2012/0314183 A1 | 12/2012 | Nakamura et al. |
| 2014/0198294 A1* | 7/2014 | Nakamura .............. A61L 27/18 351/159.04 |

FOREIGN PATENT DOCUMENTS

| | | |
|---|---|---|
| EP | 2538266 A1 | 12/2012 |
| EP | 2745854 A1 | 6/2014 |
| EP | 2746835 A1 | 6/2014 |
| JP | 54116947 A | 9/1979 |
| JP | 63246718 A | 10/1988 |
| JP | 2002047365 A | 2/2002 |
| JP | 2003171686 A | 6/2003 |
| JP | 2010508563 A | 3/2010 |
| JP | 2013533518 A | 8/2013 |
| JP | 2014533381 A | 12/2014 |
| WO | 0194454 A1 | 12/2001 |
| WO | 2013024799 A1 | 2/2013 |
| WO | 2013024800 A1 | 2/2013 |

OTHER PUBLICATIONS

International Search Report and Written Opinion for International Application No. PCT/JP2017/006615, dated Mar. 28, 2017—7 pages.
Extended European Search Report for European Application No. 17 756 540.5, dated Dec. 2, 2019, 7 pages.

* cited by examiner

*Primary Examiner* — Anna R Falkowitz
(74) *Attorney, Agent, or Firm* — Ratner Prestia

(57) ABSTRACT

A device includes a substrate and a hydrophilic polymer layer made of a hydrophilic polymer having a hydroxyl group. The hydrophilic polymer layer having a hydroxyl group is fixed to at least a part of a surface of the substrate and the hydrophilic polymer further has an amide group. A liquid film retention time of the device is 15 seconds or more. The device has a surface of a substrate which is hydrophilized. A method for producing the device by a simple method is also disclosed.

7 Claims, No Drawings

DEVICE AND PRODUCTION METHOD FOR THE SAME

CROSS REFERENCE TO RELATED APPLICATIONS

This is the U.S. National Phase application of PCT/JP2017/006615, filed Feb. 22, 2017, which claims priority to Japanese Patent Application No. 2016-030687, filed Feb. 22, 2016, the disclosures of these applications being incorporated herein by reference in their entireties for all purposes.

TECHNICAL FIELD OF THE INVENTION

The present invention relates to a hydrophilic device and a production method for the same.

BACKGROUND OF THE INVENTION

Heretofore, soft materials made of a resin such as a silicone rubber and hydrogel and hard materials such as metal and glass have been used for various purposes in various fields. Applications of soft materials include medical devices for introduction into a living body and for covering a surface of a living body, biotechnology devices such as cell culture sheets and scaffold materials for tissue regeneration, and cosmetic devices such as facial packs. Applications of hard materials include electric appliances such as personal computers, mobile phones, displays, etc., ampules for use in injections, and use as diagnostic and analysis tools such as capillaries, biosensing chips, and the like.

When various materials are introduced into a living body as a medical device or attached to a surface of a living body, in order to make it easy for adaptation to the living body, it becomes necessary to perform surface modification of materials for the purpose of improving biocompatibility such as hydrophilicity and lubricity. If it is possible to impart better properties such as hydrophilicity, lubricity, and biocompatibility than before modification, users (patients, etc.) can expect an improvement in tactile sensation, reduction of discomfort, and the like.

Various methods have been known as a method for modification of a surface of a material. In the prior art, since it was difficult to impart sufficient hydrophilicity in the case of one polymer material, there has been known a method of laminating by forming a layer of each of two or more polymer materials one by one through coating (see, for example, Patent Literature 1). Of these, a method of laminating by forming a layer of each of two or more polymer materials one by one on a layer having a charge opposite to that of the lower layer to coat layers having alternately different charges is called a layer by layer method (LbL method) or the like. In such coating obtained by the LbL method, it is considered that each layer of the material is bonded to other layer by the electrostatic interaction.

However, in a conventional LbL coating, it is common practice to laminate multilayers such as 3 to 20 layers, which may prolong the production process, leading to an increase in the production cost.

To improve cost efficiency, there has recently been disclosed, as an improved method of the LbL method, a method in which a polyionic substance and a hydrolysate substance during autoclaving are used and the polyionic substance is adsorbed onto a surface of a silicone hydrogel by a single heat treatment and, at the same time, the surface of the silicone hydrogel is hydrophilized (see Patent Literature 2).

However, the material to which the above-mentioned invention can be applied is limited to a hydrous hydrogel.

Patent Literature 3 discloses a method in which two hydrophilic polymers are crosslinked on a surface of a silicone hydrogel by a single heat treatment.

However, the applicable material is also limited to a hydrous hydrogel. Furthermore, this invention is required to include the step of crosslinking a carboxyl group-containing polymer to a surface of a silicone hydrogel before a heat treatment, and a hydrophilic polymer is crosslinked on a surface of a lens in an aqueous solution via a covalent bond between an epoxide group of a crosslinkable hydrophilic polymer material and a carboxyl group crosslinked on the surface of the silicone hydrogel surface, and thus the step may be complicated, leading to an increase in the production cost.

Patent Literatures 4 to 6 disclose surface coating of a contact lens with an ionic polymer, but the performance is insufficient.

PATENT LITERATURE

[Patent Literature 1] WO 2013/024800 A
[Patent Literature 2] JP 2010-508563 W
[Patent Literature 3] JP 2014-533381 W
[Patent Literature 4] JP 54-116947 A
[Patent Literature 5] JP 63-246718 A
[Patent Literature 6] JP 2002-047365 A

SUMMARY OF THE INVENTION

The present invention has been made in view of foregoing circumstances, and it is an object of the present invention to provide a device whose surface is hydrophilized, and a method for simply producing the same.

To achieve the above object, the present invention has the following structures.

The present invention is directed to a device including a substrate and a hydrophilic polymer layer made of a hydrophilic polymer having a hydroxyl group, wherein the hydrophilic polymer layer is fixed to at least a part of a surface of the substrate and the hydrophilic polymer having a hydroxyl group further has an amide group, and a liquid film retention time of the device is 15 seconds or more.

In another aspect, the present invention provides a device including a substrate and a hydrophilic polymer layer made of a hydrophilic polymer having a hydroxyl group, wherein the hydrophilic polymer layer is fixed to at least a part of a surface of the substrate, and at least a part of the hydrophilic polymer layer is separated into two or more layers or two or more phases.

A method for producing the device according to the present invention includes disposing a substrate in a solution containing a hydrophilic polymer having a hydroxyl group and having an initial pH of 2.0 or higher to 6.0 or lower and heating the solution.

According to the present invention, unlike the prior art, it is possible to obtain a device imparted with hydrophilicity by a simple process since a substrate surface is hydrophilized by a simple method. Applicable substrate is not limited to a hydrous hydrogel.

DETAILED DESCRIPTION OF EMBODIMENTS OF THE INTENTION

In the present invention, it is possible to use, as a substrate of the device, both a hydrous substrate and a non-hydrous substrate.

Specifically, the material of the hydrous substrate includes a hydrogel or the like. Examples of the material of the non-hydrous substrate include an acrylic resin such as polymethyl methacrylate, a silicone substrate having a siloxane bond, metal such as aluminum, and glass.

The present invention is also applicable to an ordinary hydrogel containing no silicone and a hydrogel containing silicone (silicone hydrogel) with respect to a material of a hydrous substrate. It is possible to use particularly suitably for the silicone hydrogel since surface physical properties can be significantly improved.

According to the present invention, it is possible to impart moderate elastic modulus and hydrophilicity to a surface of the device even if the substrate may be hydrous or non-hydrous.

Therefore, the moisture content of substrate may be 0 to 99% by mass. The moisture content of the substrate is preferably 0.0001% by mass or more, and most preferably 0.001% by mass or more, since the effect of imparting moderate elastic modulus and hydrophilicity to the device surface is further enhanced. The moisture content of the substrate is preferably 60% by mass or less, more preferably 50% by mass or less, and still more preferably 40% by mass or less.

In the present invention, a hydrophilic polymer layer existing on a substrate surface is a layer in which a hydrophilic polymer is formed as a layer on the substrate surface. A part of the hydrophilic gel layer may enter into the inside of the substrate.

The hydrophilicity is imparted to at least a part of a surface of the device by the existence of a polymer layer made of a hydrophilic polymer. The material constituting the polymer layer is usually a material different from that of the substrate. However, as long as a predetermined effect can be obtained, the material may be the same material as that constituting the substrate.

The polymer forming the polymer layer is composed of a material having hydrophilicity. As long as the development of the hydrophilicity is not impaired, additives other than the above material may be included. Here, the material having the hydrophilicity is a material which is soluble in 100 parts by mass of water at room temperature (20 to 23° C.) in the amount of 0.0001 part by mass or more, preferably 0.01 part by mass or more, more preferably 0.1 part by mass or more, and still more preferably 1 part by mass or more, based on 100 parts by mass of water.

A hydrophilic polymer having a hydroxyl group is used as the hydrophilic polymer. The hydrophilic polymer having a hydroxyl group is preferable because it can form a surface excellent in not only water wettability but also antifouling properties against body fluid, and the like. The hydrophilic polymer having a hydroxyl group as used herein is preferably a polymer having an acidic hydroxyl group. Specifically, a polymer having a group selected from a carboxy group and a sulfonic acid group is preferable, and a polymer having a carboxy group is most preferable. The carboxy group or the sulfonic acid group may be in the form of a salt.

Examples of the hydrophilic polymer having a hydroxyl group include polymethacrylic acid, polyacrylic acid, poly(vinylbenzoic acid), poly(thiophene-3-acetic acid), poly(4-styrenesulfonic acid), polyvinylsulfonic acid, poly(2-acrylamido-2-methylpropanesulfonic acid), and salts thereof. Those mentioned above are examples of a homopolymer, and it is also possible to suitably use a copolymer of hydrophilic monomers constituting the hydrophilic polymer, or a copolymer of the hydrophilic monomer and the other monomer.

When the hydrophilic polymer having a hydroxyl group is a copolymer, the hydrophilic monomer constituting the copolymer is preferably a monomer having a group selected from an allyl group, a vinyl group, and a (meth)acryloyl group in view of high polymerizability. The monomer having a (meth)acryloyl group is most preferable. Suitable examples of such monomer include (meth)acrylic acid, vinylbenzoic acid, styrenesulfonic acid, vinylsulfonic acid, 2-acrylamido-2-methylpropanesulfonic acid, and salts thereof. Of these, a monomer selected from (meth)acrylic acid, 2-acrylamido-2-methylpropanesulfonic acid, and salts thereof is more preferable, and a monomer selected from (meth)acrylic acid and salts thereof is most preferable.

It is preferable that the hydrophilic polymer having a hydroxyl group has an amide group, in addition to the hydroxyl group, since it can form a surface having not only water wettability but also lubricity.

Examples of the acidic hydrophilic polymer having a hydroxyl group and an amide group include polyamides having a carboxyl group, a copolymer of a monomer having a hydroxyl group and a monomer having an amide group, and the like.

Suitable examples of the polyamides having a carboxyl group include polyamino acids such as polyaspartic acid and polyglutamic acid, and polypeptides.

It is possible to suitably use, as the monomer having a hydroxyl group, a monomer selected from methacrylic acid, acrylic acid, vinylbenzoic acid, thiophene-3-acetic acid, 4-styrenesulfonic acid, vinylsulfonic acid, 2-acrylamido-2-methylpropanesulfonic acid, and salts thereof.

In view of ease of polymerization, the monomer having an amide group is preferably a monomer selected from a monomer having a (meth)acrylamide group and N-vinylcarboxylic acid amide (including cyclic one). Suitable Examples of such monomer include N-vinylpyrrolidone, N-vinylcaprolactam, N-vinylacetamide, N-methyl-N-vinylacetamide, N-vinylformamide, N,N-dimethylacrylamide, N,N-diethylacrylamide, N-isopropylacrylamide, N-(2-hydroxyethyl)acrylamide, acryloyl morpholine, and acrylamide. Of these, N-vinylpyrrolidone and N,N-dimethylacrylamide are preferable in view of the lubricity, and N,N-dimethylacrylamide is most preferable.

When the hydrophilic polymer having an amide group in addition to the hydroxyl group is a copolymer, preferred specific examples are a (meth)acrylic acid/N-vinylpyrrolidone copolymer, a (meth)acrylic acid/N,N-dimethylacrylamide copolymer, a 2-acrylamido-2-methylpropanesulfonic acid/N-vinylpyrrolidone copolymer, and a 2-acrylamido-2-methylpropanesulfonic acid/N,N-dimethylacrylamide copolymer. A (meth)acrylic acid/N,N-dimethylacrylamide copolymer is most preferable.

When using a copolymer of a monomer having a hydroxyl group and a monomer having an amide group, the copolymerization ratio thereof is preferably in a range of 1/99 to 99/1 in terms of [mass of monomer having a hydroxyl group]/[mass of monomer having an amide group]. The copolymerization ratio of the monomer having a hydroxyl group is more preferably 2% by mass or more, still more preferably 5% by mass or more, and yet more preferably 10% by mass or more. The copolymerization ratio of the monomer having a hydroxyl group is more preferably 90% by mass or less, still more preferably 80% by mass or less, and yet more preferably 70% by mass or less. The copolymerization ratio of the monomer having an amide group is more preferably 10% by mass or more, still more preferably 20% by mass or more, and yet more preferably 30% by mass or more. The copolymerization ratio of the monomer having an amide group is more preferably 98% by mass or less, still more preferably 95% by mass or less, and yet more preferably 90% by mass or less. When the copolymerization ratio is within the above range, functions such as lubricity and antifouling properties against body fluid are easily developed.

It is also possible to further copolymerize the monomer having a hydroxyl group and the monomer having an amide group with a monomer having different hydroxyl group or amide group and a monomer having neither hydroxyl group nor amide group alone or in combination.

Suitable examples of the monomer other than the above monomers include hydroxyethyl(meth)acrylate, hydroxypropyl(meth)acrylate, hydroxybutyl(meth)acrylate, hydroxyethyl(meth)acrylamide, glycerol (meth)acrylate, caprolactone-modified 2-hydroxyethyl (meth)acrylate, N-(4-hydroxyphenyl)maleimide, hydroxystyrene, and vinyl alcohol (carboxylic acid vinyl ester as a precursor). Of these, in view of ease of polymerization, a monomer having a (meth)acryloyl group is preferable and a (meth)acrylic acid ester monomer is more preferable. Of these, in view of antifouling properties against body fluid, hydroxyethyl (meth)acrylate, hydroxypropyl (meth)acrylate, and glycerol (meth)acrylate are preferable, and hydroxyethyl (meth)acrylate is most preferable. It is also possible to use a monomer having functions such as hydrophilicity, antibacterial properties, and antifouling properties.

As long as properties required to the device are not impaired, additives other than the above materials may be included in the hydrophilic polymer layer. In addition to the hydrophilic polymer having a hydroxyl group, one or more other hydrophilic polymers may be included in the hydrophilic polymer layer. Since the production method may be complicated, it is considered to be often preferable that the hydrophilic polymer layer is made of only one hydrophilic polymer having a hydroxyl group.

Here, one polymer means a polymer or a polymer group (isomers, complexes, etc.) produced by one synthesis reaction. When a copolymerized polymer is obtained by using plural monomers, even though the constituent monomer species are the same, a polymer synthesized by changing a compounding ratio is not said to be one polymer.

The expression that the hydrophilic polymer layer is made of only one hydrophilic polymer having a hydroxyl group means that the hydrophilic polymer layer does not contain any polymer other than the hydrophilic polymer having a hydroxyl group, or even if it contains the other polymer, it means that the content of the other polymer is 3 parts by mass or less based on 100 parts by mass of the hydrophilic polymer having a hydroxyl group. The content of the other polymer is more preferably 0.1 part by mass or less, and still more preferably 0.0001 part by mass or less.

In particular, when the other polymer is a basic polymer, if the content is more than the above range, a problem with transparency may occur. In the prior art, an acidic polymer and a basic polymer were used in combination to laminate a hydrophilic polymer on a surface of a substrate utilizing the electrostatic adsorption effect. However, according to the present invention, a hydrophilic polymer layer made of only one polymer can be formed on a surface of the substrate.

In the present invention, the expression that the hydrophilic polymer layer having a hydroxyl group is fixed on at least a part of the surface of the substrate means that the hydrophilic polymer layer is fixed on a surface of the substrate through chemical bond such as hydrogen bond, ionic bond, van der Waals bond, hydrophobic bond, or complex formation. The hydrophilic polymer layer may be bonded to the substrate through a covalent bond, or rather, the hydrophilic polymer layer preferably has no covalent bond with the substrate since it becomes possible to produce by a simple process.

Depending on the application, the hydrophilic polymer layer preferably exists on the entire surface of one surface of the substrate surface. In the case of a two-dimensional shape in which the substrate has no thickness or, if any, thickness can be neglected, the hydrophilic polymer layer preferably exists on the entire surface of one surface of the substrate surface. More preferably, the hydrophilic polymer layer exits on the entire surface of the substrate.

Since the hydrophilic polymer can be produced by a simple process regardless of whether the substrate is hydrous or non-hydrous, it is preferred that a covalent bond does not exist between the hydrophilic polymer and the substrate. The absence of a covalent bond is judged by having no chemically reactive group. Specific examples of the chemically reactive group include, but are not limited to, an azetidinium group, an epoxy group, an isocyanate group, an aziridine group, an azlactone group, and combinations thereof.

The thickness of the hydrophilic polymer layer is preferably 1 nm or more and less than 100 nm when observing a cross section of the device in a frozen state (hereinafter referred to as a frozen state) in a hydrous state using a scanning transmission electron microscope since it is easy to exhibit functions such as water wettability and lubricity. The thickness is more preferably 5 nm or more, still more preferably 10 nm or more, and most preferably 15 nm or more. The thickness is more preferably 90 nm or less, still more preferably 80 nm or less, and most preferably 70 nm or less. It is possible to measure the thickness of the hydrophilic polymer layer in a frozen state by scanning transmission electron microscope observation using a cryotransfer holder.

When the thickness of the polymer layer in a frozen state is 100 nm or more, for example, in the case of using for a medical device such as an ophthalmic lens, refraction of light for focusing on the retina is disturbed and poor visibility is likely to occur, unfavorably.

The thickness of the hydrophilic polymer layer in a dry state is preferably 1 to 100 nm, since functions such as water wettability and lubricity are likely to be exhibited. The thickness is more preferably 10 nm or more, and still more preferably 20 nm or more. The thickness is more preferably 90 nm or less, still more preferably 80 nm or less, and most preferably 70 nm or less. When the thickness of the hydrophilic polymer layer is 100 nm or less, the hydrophilic polymer layer is excellent in water wettability and lubricity and, for example, in the case of using for a medical device such as an ophthalmic lens, refraction of light for focusing on the retina is not disturbed and poor visibility becomes hardly occurs.

The hydrophilic polymer layer is preferably in a state of being separated into two or more layers or two or more phases.

Here, the state where the hydrophilic polymer layer is separated into two or more layers means a state where a multi-layer structure of two or more layers is observed in the hydrophilic polymer layer when a cross section of the device is observed using a transmission electron microscope. If it is difficult to judge separation of layers only by observation with a transmission electron microscope, separation of layers is judged by analyzing elements and compositions of a cross section of the device using means capable of performing elemental analysis and composition analysis, such as scanning transmission electron microscopy and electron energy-loss spectroscopy, energy dispersive X-ray spectroscopy, or time-of-flight secondary ion mass spectrometry. The state where the hydrophilic polymer layer is separated into two or more phases means a state where a state of phase separation into two or more phases in the hydrophilic polymer layer is observed when a cross section of the device is observed using a transmission electron microscope. The case where it is difficult to judge separation of phases only by observation with a transmission electron microscope is the same as mentioned above.

Two or more polymers have conventionally been required so as to form a polymer layer of two or more layers or two or more layers on a substrate surface. However, it has been found in the present invention that it is possible to form a hydrophilic polymer layer separated into two or more layers or two or more phases on a substrate surface even if only one polymer exists.

When the hydrophilic polymer layer has a multilayer structure of two or more layers, the thickness of the hydrophilic polymer layer sufficiently increases, leading to further improvement in satisfactory water wettability and lubricity. In a state where the hydrophilic polymer layer is separated into two or more phases, it becomes easy to distinguish from foreign matters such as dust when a cross section of the device is observed using a transmission electron microscope. Therefore, it is easy to confirm formation of the polymer layer on the substrate surface and is efficient for quality inspection.

In the hydrophilic polymer layer, at least a part of the hydrophilic polymer layer preferably exists in a state of being mixed with the substrate. The state where the hydrophilic polymer layer is mixed with the substrate is determined by the fact that elements derived from the substrate are detected in at least a part of the hydrophilic polymer layer when a cross section of the device is observed using observation means capable of performing elemental analysis or composition analysis, such as scanning transmission electron microscopy, electron energy-loss spectroscopy, energy dispersive X-ray spectroscopy, or time-of-flight secondary ion mass spectrometry. By mixing the hydrophilic polymer layer with the substrate, the hydrophilic polymer can be firmly fixed to the substrate.

When at least a part of the hydrophilic polymer layer exists in a state of being mixed with the substrate, it is preferred to observe a two-layer structure of a "layer in which at least a part of a hydrophilic polymer layer is mixed with a substrate" (hereinafter referred to as a "mixed layer") and a "layer made of a hydrophilic polymer (hereinafter referred to as a single layer). The thickness of the mixed layer is preferably 3% or more, more preferably 5% or more, and still more preferably 10% or more, based on the total thickness of the mixed layer and the single layer. The thickness of the mixed layer is preferably 98% or less, more preferably 95% or less, still more preferably 90% or less, and most preferably 80% or less, based on the total thickness of the mixed layer and the single layer. Too small thickness ratio of the mixed layer leads to insufficient mixing of the hydrophilic polymer with the substrate, unfavorably. Too large thickness ratio of the mixed layer may lead to insufficient development of properties of the hydrophilic polymer, unfavorably.

From the viewpoint of excellent transparency of the device, the number of layers or phases is preferably 2 to 3, and more preferably 2. If the device has high transparency, for example, when the device is used as a skin material, it is easy to visually observe the state of the skin without peeling the device from the skin. If the device has high transparency, it can be used as an ophthalmic lens or the like.

In a preferred embodiment of the present invention, the device of the present invention may be in the form of a tube. Examples of tubular devices include an infusion tube, a gas delivery tube, a drainage tube, a blood circuit, a coating tube, a catheter, a stent, a sheath, a tube connector, an access port, and the like.

In another preferred embodiment of the present invention, the device of the present invention may be in the form of a sheet or a film. Specific examples thereof include a skin covering material, a wound dressing material, a protective material for skin, a drug carrier for skin, a biosensor chip, an endoscopic dressing material, and the like.

In still another preferred embodiment of the present invention, the device of the present invention may have a storage container shape. Specific examples thereof include a drug carrier, a cuff, a drainage bag, and the like.

In yet another preferred embodiment of the present invention, the device of the present invention may have a lens shape. Specific examples thereof include ophthalmic lenses such as contact lens, intraocular lens, artificial cornea, corneal inlay, corneal onlay, eyeglass lens, and the like.

Among ophthalmic lenses, especially contact lens is one of the most preferred embodiments of the present invention.

When the device of the present invention is, for example, an ophthalmic device such as a medical device or an ophthalmic lens which is used by being attached to a surface of a living body, the liquid film retention time on the surface of the device is preferably long from the viewpoint of preventing from sticking to the skin of users and preventing from sticking to the cornea of wearers. Here, the liquid film retention time is the time period during which a liquid film on the device surface is retained without being broken when the device immersed in a phosphate buffer solution is pulled up from the liquid and kept so that the surface is vertical in the air. The liquid film retention time is preferably 15 seconds or more, more preferably 20 seconds or more, and most preferably 30 seconds or more.

When the device of the present invention is an ophthalmic device such as an ophthalmic lens, the dynamic contact angle of the device surface is preferably low from the viewpoint of preventing from sticking to the cornea of wearers. The dynamic contact angle is preferably 60° or less, more preferably 55° or less, and most preferably 50° or less. The dynamic contact angle (during advancing, immersion rate: 0.1 mm/sec) is measured using a sample wetted with a phosphate buffer solution. Details of the measuring method will be mentioned later.

When the device of the present invention is a medical device which is used by being inserted into a living body, a surface of the device preferably has excellent lubricity. An indicator representing the lubricity, the friction coefficient measured by the method mentioned in Examples of the present specification is preferably small. The friction coefficient is preferably 0.7 or less, more preferably 0.6 or less, and most preferably 0.5 or less. If the friction is extremely small, it may be difficult to handle during installing and removing, so that the friction coefficient is preferably 0.001 or more, and more preferably 0.002 or more.

When the device of the present invention is used in an ophthalmic device such as an ophthalmic lens, the moisture content change rate before and after formation of a hydrophilic polymer layer is preferably 10% by mass or less, more preferably 8% by mass or less, and most preferably 6% by mass or less, from the viewpoint of preventing poor visibility or deformation caused by distortion of a refractive index due to an increase in moisture content. Details of the measuring method will be mentioned later.

The size change rate before and after formation of the hydrophilic polymer layer of the device of the present invention is preferably 5% or less, more preferably 4 or less, and most preferably 3% or less, from the viewpoint of preventing corneal injury caused by deformation when used in an ophthalmic device such as an ophthalmic lens. Details of the measuring method will be mentioned later.

The tensile elastic modulus change rate before and after formation of the hydrophilic polymer layer of the device of the present invention is preferably 15% or less, more preferably 14% or less, and most preferably 13% or less. Too large tensile elastic modulus change rate may lead to deformation and poor tactile sensation, unfavorably. Details of the measuring method will be mentioned later.

The antifouling properties of the device of the present invention can be evaluated by the deposition of mucin and deposition of lipid (methyl palmitate). The smaller the deposition amount by these evaluations, the more tactile sensation is excellent and bacterial propagation risk is reduced, favorably. The mucin deposition amount is preferably 10 $\mu g/cm^2$ or less, more preferably 5 $\mu g/cm^2$ or less, and most preferably 3 $\mu g/cm^2$ or less. Details of the measuring method will be mentioned later.

Next, a method of manufacturing a device of the present invention will be described. The device of the present invention can be obtained by a method in which a substrate is heated in a state of being disposed in a solution containing a hydrophilic polymer having a hydroxyl group.

Here, the inventors of the present invention have found that, using an extremely simple method in which an initial pH of the solution containing a hydrophilic polymer having a hydroxyl group is adjusted to 2.0 or higher and 6.0 or lower and a substrate is disposed in the solution, and then the solution is heated in the state, the hydrophilic polymer having a hydroxyl group can be fixed to a surface of the substrate, thus imparting excellent water wettability, lubricity, and the like to the device, without using a conventionally known special method, for example, a method in which the electrostatic adsorption effect using an acidic polymer in combination with a basic polymer is utilized, leading to industrially very important meaning from the viewpoint of shortening the production process.

When a polymer layer is formed on a surface of a substrate by using only one hydrophilic polymer having a hydroxyl group, in the prior art, since the layer does not have sufficient thickness, there was a problem that sufficient water wettability and lubricity are not easily imparted to the device. Here, an increase in molecular weight of the hydrophilic polymer leads to an increase in thickness of the thus obtained polymer layer. However, too large molecular weight may lead to an increase in difficulty of handling during the production due to an increase in viscosity, and thus there is limitation on the molecular weight. An increase in concentration of a hydrophilic polymer in the solution during the production leads to an increase in thickness of the thus obtained polymer layer.

However, too large concentration may lead to an increase in difficulty of handling during the production due to an increase in viscosity, and thus there is also limitation on the concentration. However, regardless of only one hydrophilic polymer having a hydroxyl group in the present invention, in the case of having a multi-layer structure of two or more layers on a substrate surface, it becomes possible to increase the thickness of the layer even if a polymer having a molecular weight in the below-mentioned range is used and the concentration is set in the below-mentioned range, thus making it easy to achieve sufficient water wettability and lubricity.

The hydrophilic polymer having a hydroxyl group used in the present invention preferably has a molecular weight of 2,000 to 1,500,000. The molecular weight is more preferably 5,000 or more, and still more preferably 10,000 or more. The molecular weight is more preferably 1,200,000 or less, and still more preferably 1,000,000 or less. Here, a weight average molecular weight in terms of polyethylene glycol measured by a gel permeation chromatography method (aqueous solvent) is used as the molecular weight.

An increase in concentration of the hydrophilic polymer in the solution during the production leads to an increase in thickness of the thus obtained hydrophilic polymer layer. However, too high concentration of the hydrophilic polymer may lead to an increase in difficulty of handling during the production due to an increase in viscosity, so that the concentration in the solution of the hydrophilic polymer having a hydroxyl group is preferably 0.0001 to 30% by mass. The concentration of the hydrophilic polymer is more preferably 0.001% by mass or more, and still more preferably 0.005% by mass or more. The concentration of the hydrophilic polymer is more preferably 20% by mass or less, and still more preferably 15% by mass or less.

In the above process, the initial pH value of the solution containing a hydrophilic polymer is preferably 2.0 to 6.0 since turbidity does not occur in the solution to obtain a device having satisfactory transparency. The initial pH is more preferably 2.2 or higher, still more preferably 2.4 or higher, still more preferably 2.5 or higher, and most preferably 2.6 or higher. The initial pH is preferably 5.0 or lower, more preferably 4.5 or lower, and most preferably 4.0 or lower. If the initial pH is 2.0 or higher, turbidity of the solution is less likely to occur. It is preferred that turbidity does not occur in the solution because the surface of the device may have high water wettability and lubricity. When the initial pH is higher than 6.0, the thus obtained hydrophilic polymer layer may not be separated into two or more layers or two or more phases, leading to deterioration of water wettability and lubricity of the surface of the device, unfavorably.

The pH of the solution can be measured using a pH meter (e.g., pH meter Eutech pH 2700 (Eutech Instruments)). Here, the initial pH of a solution containing a hydrophilic polymer having a hydroxyl group means the pH value of the solution measured after adding all the hydrophilic polymer to the solution, followed by stirring at room temperature (23 to 25° C.) for 2 hours with a rotor to thereby make the solution uniform, before disposing a substrate and heating the substrate. In the present invention, the pH value is rounded off to one decimal place.

The pH of the solution can change when a heating operation is performed. The pH of the solution after the heating operation is more preferably 2.0 to 6.5. The pH after heating is more preferably 2.2 or higher, still more preferably 2.3 or higher, and most preferably 2.4 or higher. The pH after heating is more preferably 5.9 or lower, still more preferably 5.5 or lower, yet more preferably 5.0 or lower, and most preferably 4.5 or lower. When the pH of the solution after the heating operation is in the above range, appropriate pH conditions can be obtained while performing the heating operation, thus obtaining suitable physical properties of the thus obtained device. After modifying the device surface by performing the heating operation according to the present invention, the pH can be adjusted by performing a neutralization treatment or adding water. The pH of the solution after performing the heating operation as used herein is the pH before performing such pH adjustment.

A solvent of the solution containing a hydrophilic polymer having a hydroxyl group is preferably water. The pH of the solution is adjusted by adding an acidic substance such as acetic acid, citric acid, formic acid, ascorbic acid, trifluoromethanesulfonic acid, methanesulfonic acid, nitric acid, sulfuric acid, phosphoric acid, or hydrochloric acid to a solution containing a hydrophilic polymer. Of these, citric acid, ascorbic acid, and sulfuric acid are preferable from the viewpoint of low volatility and high safety to a living body. To make it easy to finely adjust the pH, a buffering agent is preferably added to the solution.

It is possible to use, as the buffering agent, any physiologically compatible known buffering agent. An appropriate buffering agent in the present invention is known to a person with an ordinary skill in the art, and examples thereof include boric acid, borate (e.g., sodium borate), citric acid, citrates (e.g., potassium citrate), bicarbonate (e.g., sodium bicarbonate), phosphate buffer solution (e.g., $Na_2HPO_4$, $NaH_2PO_4$, and $KH_2PO_4$), TRIS (tris(hydroxymethyl)aminomethane), 2-bis(2-hydroxyethyl)amino-2-(hydroxymethyl)-1,3-propanediol, bis-aminopolyol, triethanolamine, ACES (N-(2-acetamide)-2-aminoethanesulfonic acid), BES (N,N-bis(2-hydroxyethyl)-2-aminoethanesulfonic acid), HEPES (4-(2-hydroxyethyl)-1-piperazineethanesulfonic acid), MES (2-(N-morpholino)ethanesulfonic acid), MOPS (3-[N-morpholino]-propanesulfonic acid), PIPES (piperazine-N,N'-bis(2-ethanesulfonic acid)), TES (N-[tris(hydroxymethyl)methyl]-2-aminoethanesulfonic acid), and salts thereof. Each buffering agent is used in the effective amount required to achieved desired pH and exists in the solution in the amount of 0.001% by mass to 2% by mass, preferably 0.01% by mass to 1% by mass, and more preferably 0.05% by mass to 0.30% by mass. The amount may be in a range of a combination of either the upper limit or the lower limit.

Examples of the heating method include a high-pressure steam sterilization method, irradiation with electromagnetic waves (γ ray, microwave, etc.), a dry heat method, a flame method, and the like.

From the viewpoint of the water wettability, lubricity, and shortening of the production process, a high-pressure steam sterilization method is most preferable. An autoclave is preferably used as an apparatus.

The heating temperature is preferably 60° C. to 200° C. from the viewpoint of obtaining a device surface exhibiting satisfactory water wettability and lubricity and exerting less influence on the strength of the device itself. The heating temperature is more preferably 80° C. or higher, still more preferably 100° C. or higher, yet more preferably 101° C. or higher, and most preferably 110° C. or higher. The heating temperature is more preferably 180° C. or lower, still more preferably 170° C. or lower, and most preferably 150° C. or lower.

If the heating time is too short, a device surface exhibiting satisfactory water wettability and lubricity cannot be obtained. Meanwhile, if the heating time is too long, an adverse influence is exerted on the strength of the device itself, the heating time is preferably 5 minutes to 600 minutes. The heating time is more preferably 10 minutes or more, and still More preferably 15 minutes or more. The heating time is more preferably 400 minutes or less, and still more preferably 300 minutes or less.

After the above heat treatment, the device thus obtained may be further subjected to the other treatment. Examples of the other treatment include treatments of methods such as a method in which a similar heat treatment is performed in a solution containing a hydrophilic polymer having a hydroxyl group, a method in which a similar heat treatment is performed by using a solution containing no hydrophilic polymer in place of the solution, a method in which irradiation with radiation is performed, a method of performing a layer by layer treatment (LbL treatment) in which each material having an opposite charge is alternately coated one by one, a method in which a crosslinking treatment with metal ions is performed, a method in which a chemical crosslinking treatment is performed, and the like. However, in light of the idea of the present invention which enables hydrophilization of a substrate surface by a simple method, a treatment is preferably performed as long as the production process does not become too complicated.

Radiations used for the above irradiation with radiation are preferably various ion beams, electron beams, positron beams, X-rays, γ rays, and neutron rays, more preferably electron rays and γ rays, and most preferably γ rays.

As the above LbL treatment, for example, a treatment using an acidic polymer and a basic polymer as mentioned in WO 2013/024800 A is preferably used.

Metal ions used for the above crosslinking treatment with metal ions are preferably various metal ions, more preferably monovalent and divalent metal ions, and most preferably divalent metal ions. Alternatively, a chelate complex may also be used.

As the above chemical crosslinking treatment, for example, a reaction between an epoxide group and a carboxyl group as mentioned in JP 2014-533381 A and a crosslinking treatment formed between known appropriate acidic hydrophilic polymers having a hydroxyl group may be used.

In the above method in which a similar heat treatment is performed by using a solution containing no hydrophilic polymer in place of the solution, the solution containing no hydrophilic polymer is not particularly limited and a buffering agent solution is preferable. The above-mentioned substances can be used as the buffering agent.

The pH of the buffering agent solution is preferably within a physiologically acceptable range of 6.3 to 7.8. The pH of the buffering agent solution is preferably 6.5 or higher, and still more preferably 6.8 or higher. The pH of the buffering agent solution is preferably 7.6 or lower, and more preferably 7.4 or lower.

EXAMPLES

The present invention will be described more specifically by way of Examples, but the present invention is not limited to these Examples.

Analytical Method and Evaluation Method

<Water Wettability (Liquid Film Retention Time)>

A device was lightly washed in 100 mL of a phosphate buffer solution in a beaker at room temperature and then immersed in 100 mL of a fresh phosphate buffer solution for 24 hours or more. The device was pulled up from the phosphate buffer solution and the time during which the liquid film on the surface was retained in the case of keeping in the air was visually observed, and an average of N=3 was judged according to the following criteria.

A: A liquid film on a surface is retained for 20 seconds or more.

B: A liquid film on a surface disappears after 15 seconds or more and less than 20 seconds.

C: A liquid film on a surface disappears after 5 seconds or less than 15 seconds.

D: A liquid film on a surface disappears after 1 second or more and less than 5 seconds.

E: A liquid film on a surface instantly disappears (less than 1 second).

<Lubricity>

A device was lightly washed in 100 mL of a phosphate buffer solution in a beaker at room temperature and then immersed in 100 mL of a fresh phosphate buffer solution for 24 hours or more. The device was pulled up from the phosphate buffer solution and subjected to sensory evaluation when rubbing with a human finger five times (N=1).

A: There is extremely excellent lubricity (finger slides to flow on a device surface and feel no resistance).

B: There is lubricity intermediate between A and C.

C: There is moderate lubricity (finger slides on a device surface and hardly feels resistance).

D: Almost no lubricity (intermediate between C and E).

E: No lubricity (finger does not easily slide on a device surface and feel large resistance).

<Moisture Content of Substrate and Device>

A substrate was immersed in a phosphate buffer solution and left to stand at room temperature for 24 hours or more. The substrate was pulled out from the phosphate buffer solution and, after wiping off the surface moisture with a wiping cloth ("Kimwipes" (registered trademark) manufactured by NIPPON PAPER CRECIA CO., LTD.), the mass (Ww) of the substrate was measured. Thereafter, the substrate was dried at 40° C. for 2 hours in a vacuum dryer and the mass (Wd) was measured. From these masses, the moisture content of the substrate was calculated by the following formula (1). The case where the obtained value was less than 1% was judged as below the measurement limit, and the column in the table was filled with "less than 1%". An average of N=3 was regarded as the moisture content. The moisture content of the device after the fixation of the hydrophilic polymer layer was also calculated in the same manner.

$$\text{Moisture content (\%) of substrate} = 100 \times (Ww - Wd)/Ww \quad \text{Formula (1)}.$$

<Moisture Content Change Rate Before and after Fixation of Hydrophilic Polymer Layer>

The moisture content change rate was calculated by the following formula (2). An average of N=3 was regarded as the moisture content change rate before and after fixation of the hydrophilic polymer layer.

$$\text{Moisture content change rate (\% by mass) before and after fixation of hydrophilic polymer layer} = \text{moisture content (\% by mass) of device after fixation of hydrophilic polymer layer} - \text{moisture content (\% by mass) of substrate before fixation of hydrophilic polymer layer} \quad \text{Formula (2)}$$

<Contact Angle>

Using, as a sample, a strip-shaped test piece measuring about 5 mm×10 mm×0.1 mm cut out from a sample having a contact lens shape, a dynamic contact angle during advancing to a phosphate buffer solution was measured by a wettability test machine WET-6200 (manufactured by RHESCA CO., LTD.). An immersion rate was 0.1 mm/sec, and an immersion depth was 7 mm.

<Friction Coefficient>

The friction coefficient of the device surface wetted with a phosphate buffer solution (preservation solution in a package in the case of measuring a commercial available contact lens) was measured with N=5 and an average was regarded as the friction coefficient.

Apparatus: Friction tester KES-SE (manufactured by Kato Tech Co., Ltd.)

Friction SENS: H

Measurement SPEED: 2×1 mm/sec

Friction load: 44 g

<Lipid Deposition Amount>

In a 20 cc screw tube, 0.03 g of methyl palmitate, 10 g of pure water, and 1 sample having a contact lens shape were placed. The screw tube was shaken for 3 hours under the conditions at 37° C. and 165 rpm. After shaking, the sample in the screw tube was scrubbed with tap water at 40° C. and a household liquid detergent ("Mama Lemon (registered trademark)" manufactured by Lion Corporation). The washed sample was placed in a screw tube containing a phosphate buffer solution and stored in a refrigerator at 4° C. for 1 hour. Thereafter, the sample was visually observed, and if the turbid portion exists, it was judged that methyl palmitate is deposited and the area of the portion in which methyl palmitate is deposited to the entire surface of the sample was observed.

<Mucin Deposition Amount>

A test piece having a width (minimum portion) of 5 mm and a length of 14 mm was cut out from a sample having a contact lens shape using a specified punching die. Mucin Bovine Submaxillary Gland (Catalog No. 499643) available from CALBIOCHEM was used as mucin. The test piece was immersed in an aqueous mucin solution having a concentration of 0.1% under the conditions for 20 hours at 37° C., and then the amount of mucin deposited to the sample was determined by the bicinchoninic acid (BCA) protein assay method. An average of N=3 was regarded as the mucin deposition amount.

<Tensile Elastic Modulus>

A test piece having a width (minimum part) of 5 mm and a length of 14 mm was cut out from a sample having a contact lens shape using a specified punching die. Using the test piece, a tensile test was performed using Tensilon Model RTG-1210 manufactured by A&D Company, Limited. A pulling rate was 100 mm/min and a distance between grips (initial) was 5 mm. Measurements were made on a substrate before the fixation of a hydrophilic polymer layer, and a device before and after the fixation of a hydrophilic polymer layer. Measurement was made with N=8 and an average of N=6 excluding maximum and minimum was regarded as the tensile elastic modulus.

<Tensile Elastic Modulus Change Rate Before and after Fixation of Hydrophilic Polymer Layer>

The tensile elastic modulus change rate was calculated by the following formula (3). An average of N=6 was regarded as the tensile elastic modulus change rate by coating.

$$\text{Tensile elastic modulus change rate (\%) before and after fixation of hydrophilic polymer layer} = (\text{tensile elastic modulus of device after fixation of hydrophilic polymer layer} - \text{tensile elastic modulus of substrate before fixation of hydrophilic polymer layer})/\text{tensile elastic modulus of substrate before fixation of hydrophilic polymer layer} \times 100 \quad \text{Formula (3)}.$$

<Size>

The diameter of a sample having a contact lens shape was measured and an average of N=3 was regarded as the size.

<Size Change Rate Before and after Fixation of Hydrophilic Polymer Layer>

The size change rate before and after the fixation of a hydrophilic polymer layer was calculated by the following formula (4). An average of N=3 was regarded as the size change rate by coating.

Size change rate (%) before and after fixation of hydrophilic polymer layer=(size of device after fixation of hydrophilic polymer layer−size of substrate before fixation of hydrophilic polymer layer)/size of substrate before fixation of hydrophilic polymer layer×100    Formula (4).

<Molecular Weight Measurement>

The molecular weight of a hydrophilic polymer used was measured under the following conditions.
(GPC Measurement Conditions)
Apparatus: Prominence GPC system manufactured by Shimadzu Corporation
  Pump: LC-20AD
  Autosampler: SIL-20AHT
  Column oven: CTO-20A
  Detector: RID-10A
  Column: GMPWXL manufactured by Tosoh Corporation (7.8 mm in inner diameter×30 cm, particle diameter of 13 μm)
  Solvent: water/methanol=1/1 (0.1N lithium nitrate is added)
  Flow rate: 0.5 mL/minute
  Measurement time: 30 minutes
  Sample concentration: 0.1% by mass
  Injection amount: 100 μL
  Standard sample: Polyethylene oxide standard sample manufactured by Agilent Technologies, Inc. (0.1 kD to 1258 kD)

<pH Measurement Method>

The pH of the solution was measured using a pH meter Eutech pH 2700 (Eutech Instruments). In the table, the initial pH of a solution containing a hydrophilic polymer having a hydroxyl group was determined by adding all the hydrophilic polymer to the solution mentioned in each Example, followed by stirring at room temperature (23 to 25° C.) for 2 hours with a rotor to thereby make the solution uniform. In the table, "pH after heat treatment" is the pH measured immediately after the solution was cooled to room temperature (23 to 25° C.) after a heat treatment was performed once.

<Judgment of Separation of Hydrophilic Polymer Layer>

Judgment was made whether or not a hydrophilic polymer layer was separated into two or more layers by observing a cross section of a device using a transmission electron microscope.
Apparatus: Transmission electron microscope (H-7100FA manufactured by Hitachi, Ltd.)
Condition: Accelerating voltage of 100 kV
Sample preparation: Silicone-containing substrate (method of staining ultrathin section with $RuO_4$), Hydrogel substrate (method of staining ultrathin section with $OsO_4$ or method of staining ultrathin section with $RuO_4$).

<Elemental Composition Analysis of Hydrophilic Polymer Layer>

Elemental composition analysis of a hydrophilic polymer layer was performed by analyzing a cross section of a device frozen in a hydrous state using a cryo-transfer holder by a scanning transmission electron microscope and electron energy loss spectroscopy.
Apparatus: Field emission electron microscope (JEM-2100F manufactured by JEOL, Ltd.)
Acceleration voltage: 200 kV
Measurement temperature: about −100° C.
Electron energy-loss spectroscopy: GATAN GIF Tridiem
Image acquisition: Digital Micrograph
Sample preparation: method of staining frozen ultrathin section with $RuO_4$ <Film Thickness of Hydrophilic Polymer Layer>

The film thickness of a hydrophilic polymer layer in a dry state was measured by observing a cross section of a device in a dry state using a transmission electron microscope. Measurement was made under the conditions mentioned in aforementioned <Judgment of Separation of Hydrophilic Polymer Layer>. While changing seven places, the film thickness was measured at five places for each field of view, and the film thickness was measured at 35 places in total. The minimum value and the maximum value of the measured film thickness are described.

The film thickness of a hydrophilic polymer layer in a frozen state was obtained by observing a cross section of the device frozen in a water-containing state using a cryotransfer holder using a scanning transmission electron microscope. Measurement was made under the conditions mentioned in aforementioned <Elemental Composition Analysis of Hydrophilic Polymer Layer>. While changing seven places, the film thickness was measured at five places for each field of view, and the film thickness was measured at 35 places in total. The minimum value and the maximum value of the measured film thickness are described.

Reference Example 1

After preparing 28 parts by mass of a polydimethylsiloxane having a methacryloyl group at both ends represented by the formula (M1) (FM 7726, JNC Corporation, Mw: 30,000), 7 parts by mass of a silicone monomer represented by the formula (M2), 57.9 parts by mass of trifluoroethyl acrylate ("Viscoat" (registered trademark) 3F, Osaka Organic Chemical Industry Ltd.), 7 parts by mass of 2-ethylhexyl acrylate (Tokyo Chemical Industry Co., Ltd.), and 0.1 part by mass of dimethylaminoethyl acrylate (Kohjin Co., Ltd.), preparing 5,000 ppm of a photoinitiator "IRGACURE" (registered trademark) 819 (NAGASE & CO., LTD.), 5,000 ppm of a UV absorber (RUVA-93, Otsuka Chemical Co., Ltd.), and 100 ppm of a colorant (RB 246, Arran chemical) based on the total amount of these monomers, and preparing 10 parts by mass of t-amyl alcohol based on 100 parts by mass of the total amount of these monomers, all components were mixed, followed by stirring. The mixture thus obtained by stirring was filtered through a membrane filter (pore diameter: 0.45 μm) to remove insoluble substances to obtain a monomer mixture.

The above monomer mixture was poured into a contact lens mold made of a transparent resin (material on base curve side: polypropylene, material on front curve side: polypropylene) and then polymerized by irradiation with light (wavelength 405 nm (±5 nm), illuminance: 0 to 0.7 $mW/cm^2$, for 30 minutes).

After the polymerization, the molded body thus obtained was immersed in an aqueous 100% by mass isopropyl alcohol solution at 60° C. for 1.5 hours together with the mold from which a front curve and a base curve were released, and then a molded body having a contact lens shape was removed from the mold. The molded body thus obtained was immersed in a large excess amount of an aqueous 100% by mass isopropyl alcohol solution maintained at 60° C. for 2 hours to extract impurities such as residual monomers. Thereafter, the molded body was dried at room temperature (23° C.) for 12 hours.

[Chemical Formula 1]

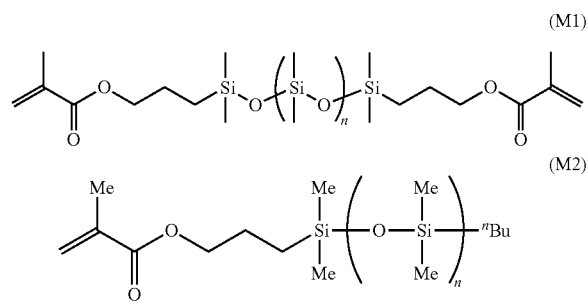

[Phosphate Buffer]

Each composition of the phosphate buffer solutions used in the processes of the following Examples and Comparative Examples and the above-mentioned measurements is as follows.
KCl: 0.2 g/L
$KH_2PO_4$: 0.2 g/L
NaCl: 8.0 g/L
$Na_2HPO_4$ (anhydrous): 1.15 g/L
EDTA: 0.25 g/L Example 1

The molded body obtained in Reference Example 1 was used as a substrate. The substrate was immersed in a solution containing 0.2% by mass of an acrylic acid/N,N-dimethylacrylamide copolymer (molar ratio in copolymerization: 1/9, Mw: 800,000, manufactured by Osaka Organic Chemical Industry Ltd.) in pure water, which has the pH of 2.6 adjusted with sulfuric acid, followed by heating in an autoclave at 121° C. for 30 minutes. The molded body thus obtained was washed with a phosphate buffer solution while shaking at 250 rpm for 30 seconds. After replacing the phosphate buffer solution by a fresh phosphate buffer solution, the molded body was further heated in the autoclave at 121° C. for 30 minutes. The results obtained by evaluation of the molded body using the above method are shown in Tables 1 to 3.

Example 2

The molded body obtained in Reference Example 1 was used as a substrate. The substrate was immersed in a solution containing 0.2% by mass of an acrylic acid/N,N-dimethylacrylamide copolymer (molar ratio in copolymerization: 1/9, Mw: 700,000, manufactured by Osaka Organic Chemical Industry Ltd.) in a phosphate buffer solution, which has the pH of 2.7 adjusted with sulfuric acid, followed by heating in an autoclave at 121° C. for 30 minutes. The molded body thus obtained was washed with a phosphate buffer solution while shaking at 250 rpm for 10 seconds. After replacing the phosphate buffer solution by a fresh phosphate buffer solution, the molded body was further heated in the autoclave at 121° C. for 30 minutes. The results obtained by evaluation of the molded body using the above method are shown in Tables 1 to 3.

Example 3

The molded body obtained in Reference Example 1 was used as a substrate. The substrate was immersed in a solution containing 0.03% by mass of an acrylic acid/N,N-dimethylacrylamide copolymer (molar ratio in copolymerization: 1/2, Mw: 500,000, manufactured by Osaka Organic Chemical Industry Ltd.) in a phosphate buffer solution, which has the pH of 3.1 adjusted with sulfuric acid, followed by heating in an autoclave at 121° C. for 30 minutes. The molded body thus obtained was washed with a phosphate buffer solution while shaking at 250 rpm for 10 seconds. After replacing the phosphate buffer solution by a fresh phosphate buffer solution, the molded body was further heated in the autoclave at 121° C. for 30 minutes. The results obtained by evaluation of the molded body using the above method are shown in Tables 1 to 3.

Example 4

The molded body obtained in Reference Example 1 was used as a substrate. The substrate was immersed in a solution containing 0.2% by mass of an acrylic acid/N,N-dimethylacrylamide copolymer (molar ratio in copolymerization: 1/9, Mw: 800,000, manufactured by Osaka Organic Chemical Industry Ltd.) in a phosphate buffer solution, which has the pH of 2.4 adjusted with sulfuric acid, followed by heating in an autoclave at 80° C. for 30 minutes. The molded body thus obtained was washed with a phosphate buffer solution while shaking at 250 rpm for 10 seconds. After replacing the phosphate buffer solution by a fresh phosphate buffer solution, the molded body was further heated in the autoclave at 121° C. for 30 minutes. The results obtained by evaluation of the molded body using the above method are shown in Tables 1 to 3.

Example 5

The molded body obtained in Reference Example 1 was used as a substrate. The substrate was immersed in a solution containing 0.2% by mass of an acrylic acid/N,N-dimethylacrylamide copolymer (molar ratio in copolymerization: 1/9, Mw: 800,000, manufactured by Osaka Organic Chemical Industry Ltd.) in a phosphate buffer solution, which has the pH of 2.4 adjusted with sulfuric acid, followed by heating in an autoclave at 100° C. for 30 minutes. The molded body thus obtained was washed with a phosphate buffer solution while shaking at 250 rpm for 10 seconds. After replacing the phosphate buffer solution by a fresh phosphate buffer solution, the molded body was further heated in the autoclave at 121° C. for 30 minutes. The results obtained by evaluation of the molded body using the above method are shown in Tables 1 to 3.

Example 6

The molded body obtained in Reference Example 1 was used as a substrate. The substrate was immersed in a solution containing 0.2% by mass of an acrylic acid/N,N-dimethylacrylamide copolymer (molar ratio in copolymerization: 1/9, Mw: 800,000, manufactured by Osaka Organic Chemical Industry Ltd.) in pure water, which has the pH of 2.4 adjusted with sulfuric acid, followed by heating in an autoclave at 121° C. for 30 minutes. The molded body thus obtained was washed with a phosphate buffer solution while shaking at 250 rpm for 10 seconds. After replacing the phosphate buffer solution by a fresh phosphate buffer solution, the molded body was further heated in the autoclave at 121° C. for 30 minutes. The results obtained by evaluation of the molded body using the above method are shown in Tables 1 to 3.

Example 7

A commercially available hydrogel lens containing 2-hydroxyethyl methacrylate as a main component "1-Day Acuvue (registered trademark)" (manufactured by Johnson & Johnson) was used as a substrate. The substrate was immersed in a solution containing 0.1% by mass of an acrylic acid/vinylpyrrolidone copolymer (molar ratio in copolymerization: 1/4, Mw: 500,000, manufactured by Osaka Organic Chemical Industry Ltd.) in a phosphate buffer solution, which has the pH of 3.1 adjusted with sulfuric acid, followed by heating in an autoclave at 121° C. for 30 minutes. The molded body thus obtained was washed with a phosphate buffer solution while shaking at 250 rpm for 10 seconds. After replacing the phosphate buffer solution by a fresh phosphate buffer solution, the molded body was further heated in the autoclave at 121° C. for 30 minutes. The results obtained by evaluation of the molded body using the above method are shown in Tables 1 to 3.

Example 8

A commercially available hydrogel lens containing 2-hydroxyethyl methacrylate as a main component "1-Day Acuvue (registered trademark)" (manufactured by Johnson & Johnson) was used as a substrate. The substrate was immersed in a solution containing 0.1% by mass of an acrylic acid/vinylpyrrolidone copolymer (molar ratio in copolymerization: 1/4, Mw: 500,000, manufactured by Osaka Organic Chemical Industry Ltd.) in a phosphate buffer solution, which has the pH of 4.1 adjusted with sulfuric acid, followed by heating in an autoclave at 121° C. for 30 minutes. The molded body thus obtained was washed with a phosphate buffer solution while shaking at 250 rpm for 10 seconds. After replacing the phosphate buffer solution by a fresh phosphate buffer solution, the molded body was further heated in the autoclave at 121° C. for 30 minutes. The results obtained by evaluation of the molded body using the above method are shown in Tables 1 to 3.

Example 9

A commercially available hydrogel lens containing 2-hydroxyethyl methacrylate as a main component "1-Day Acuvue (registered trademark)" (manufactured by Johnson & Johnson) was used as a substrate. The substrate was immersed in a solution containing 0.1% by mass of an acrylic acid/vinylpyrrolidone copolymer (molar ratio in copolymerization: 1/4, Mw: 500,000, manufactured by Osaka Organic Chemical Industry Ltd.) in a phosphate buffer solution, which has the pH of 5.0 adjusted with sulfuric acid, followed by heating in an autoclave at 121° C. for 30 minutes. The molded body thus obtained was washed with a phosphate buffer solution while shaking at 250 rpm for 10 seconds. After replacing the phosphate buffer solution by a fresh phosphate buffer solution, the molded body was further heated in the autoclave at 121° C. for 30 minutes. The results obtained by evaluation of the molded body using the above method are shown in Tables 1 to 3.

Example 10

A commercially available hydrogel lens containing 2-hydroxyethyl methacrylate as a main component "1-Day Acuvue (registered trademark)" (manufactured by Johnson & Johnson) was used as a substrate. The substrate was immersed in a solution containing 0.1% by mass of an acrylic acid/vinylpyrrolidone copolymer (molar ratio in copolymerization: 1/4, Mw: 500,000, manufactured by Osaka Organic Chemical Industry Ltd.) in a phosphate buffer solution, which has the pH of 5.7 adjusted with sulfuric acid, followed by heating in an autoclave at 121° C. for 30 minutes. The molded body thus obtained was washed with a phosphate buffer solution while shaking at 250 rpm for 10 seconds. After replacing the phosphate buffer solution by a fresh phosphate buffer solution, the molded body was further heated in the autoclave at 121° C. for 30 minutes. The results obtained by evaluation of the molded body using the above method are shown in Tables 1 to 3.

Example 11

A commercially available hydrogel lens containing 2-hydroxyethyl methacrylate as a main component "1-Day Acuvue (registered trademark)" (manufactured by Johnson & Johnson) was used as a substrate. The substrate was immersed in a solution containing 0.2% by mass of an acrylic acid/N,N-dimethylacrylamide copolymer (molar ratio in copolymerization: 1/9, Mw: 800,000, manufactured by Osaka Organic Chemical Industry Ltd.) in a phosphate buffer solution, which has the pH of 3.3 adjusted with sulfuric acid, followed by heating in an autoclave at 121° C. for 30 minutes. The molded body thus obtained was washed with a phosphate buffer solution while shaking at 250 rpm for 10 seconds. After replacing the phosphate buffer solution by a fresh phosphate buffer solution, the molded body was further heated in the autoclave at 121° C. for 30 minutes. The results obtained by evaluation of the molded body using the above method are shown in Tables 1 to 3.

Example 12

A commercially available hydrogel lens containing 2-hydroxyethyl methacrylate as a main component "1-Day Acuvue (registered trademark)" (manufactured by Johnson & Johnson) was used as a substrate. The substrate was immersed in a solution containing 0.2% by mass of an acrylic acid/N,N-dimethylacrylamide copolymer (molar ratio in copolymerization: 1/9, Mw: 500,000, manufactured by Osaka Organic Chemical Industry Ltd.) in a phosphate buffer solution, which has the pH of 3.0 adjusted with sulfuric acid, followed by heating in an autoclave at 121° C. for 30 minutes. The molded body thus obtained was washed with a phosphate buffer solution while shaking at 250 rpm for 10 seconds. After replacing the phosphate buffer solution by a fresh phosphate buffer solution, the molded body was further heated in the autoclave at 121° C. for 30 minutes. The results obtained by evaluation of the molded body using the above method are shown in Tables 1 to 3.

Example 13

A commercially available hydrogel lens containing 2-hydroxyethyl methacrylate as a main component "1-Day Acuvue (registered trademark)" (manufactured by Johnson & Johnson) was used as a substrate. The substrate was immersed in a solution containing 0.2% by mass of an acrylic acid/N,N-dimethylacrylamide copolymer (molar ratio in copolymerization: 1/2, Mw: 700,000, manufactured by Osaka Organic Chemical Industry Ltd.) in a phosphate buffer solution, which has the pH of 3.0 adjusted with sulfuric acid, followed by heating in an autoclave at 121° C. for 30 minutes. The molded body thus obtained was washed with a phosphate buffer solution while shaking at 250 rpm for 10 seconds. After replacing the phosphate buffer solution by a fresh phosphate buffer solution, the molded body was further heated in the autoclave at 121° C. for 30 minutes. The results obtained by evaluation of the molded body using the above method are shown in Tables 1 to 3.

Example 14

A commercially available hydrogel lens containing 2-hydroxyethyl methacrylate as a main component "1-Day Acuvue (registered trademark)" (manufactured by Johnson & Johnson) was used as a substrate. The substrate was immersed in a solution containing 0.1% by mass of an acrylic acid/vinylpyrrolidone copolymer (molar ratio in copolymerization: 1/4, Mw: 500,000, manufactured by Osaka Organic Chemical Industry Ltd.) in a phosphate buffer solution, which has the pH of 4.0 adjusted with sulfuric acid, followed by heating in an autoclave at 121° C. for 30 minutes. The molded body thus obtained was washed with a phosphate buffer solution while shaking at 250 rpm for 10 seconds. After replacing the phosphate buffer solution by a fresh phosphate buffer solution, the molded body was further heated in the autoclave at 121° C. for 30 minutes. The results obtained by evaluation of the molded body using the above method are shown in Tables 1 to 3.

Example 15

A commercially available hydrogel lens containing 2-hydroxyethyl methacrylate as a main component "1-Day Acuvue (registered trademark)" (manufactured by Johnson & Johnson) was used as a substrate. The substrate was immersed in a solution containing 0.1% by mass of an acrylic acid/vinylpyrrolidone copolymer (molar ratio in copolymerization: 1/4, Mw: 800,000, manufactured by Osaka Organic Chemical Industry Ltd.) in a phosphate buffer solution, which has the pH of 4.0 adjusted with sulfuric acid, followed by heating in an autoclave at 121° C. for 30 minutes. The molded body thus obtained was washed with a phosphate buffer solution while shaking at 250 rpm for 10 seconds. After replacing the phosphate buffer solution by a fresh phosphate buffer solution, the molded body was further heated in the autoclave at 121° C. for 30 minutes. The results obtained by evaluation of the molded body using the above method are shown in Tables 1 to 3.

Example 16

A commercially available hydrogel lens containing 2-hydroxyethyl methacrylate as a main component "1-Day Acuvue (registered trademark)" (manufactured by Johnson & Johnson) was used as a substrate. The substrate was immersed in a solution containing 0.1% by mass of an acrylic acid/vinylpyrrolidone copolymer (molar ratio in copolymerization: 1/9, Mw: 400,000, manufactured by Osaka Organic Chemical Industry Ltd.) in a phosphate buffer solution, which has the pH of 4.0 adjusted with sulfuric acid, followed by heating in an autoclave at 121° C. for 30 minutes. The molded body thus obtained was washed with a phosphate buffer solution while shaking at 250 rpm for 10 seconds. After replacing the phosphate buffer solution by a fresh phosphate buffer solution, the molded body was further heated in the autoclave at 121° C. for 30 minutes. The results obtained by evaluation of the molded body using the above method are shown in Tables 1 to 3.

Example 17

A commercially available silicone hydrogel lens containing polyvinylpyrrolidone and silicone as main components "1-Day Acuvue TruEye (registered trademark)" (manufactured by Johnson & Johnson) was used as a substrate. The substrate was immersed in a solution containing 0.2% by mass of an acrylic acid/N,N-dimethylacrylamide copolymer (molar ratio in copolymerization: 1/9, Mw: 800,000, manufactured by Osaka Organic Chemical Industry Ltd.) in a phosphate buffer solution, which has the pH of 3.0 adjusted with sulfuric acid, followed by heating in an autoclave at 121° C. for 30 minutes. The molded body thus obtained was washed with a phosphate buffer solution while shaking at 250 rpm for 10 seconds. After replacing the phosphate buffer solution by a fresh phosphate buffer solution, the molded body was further heated in the autoclave at 121° C. for 30 minutes. The results obtained by evaluation of the molded body using the above method are shown in Tables 1 to 3.

Example 18

A commercially available silicone hydrogel lens containing polyvinylpyrrolidone and silicone as main components "1-Day Acuvue TruEye (registered trademark)" (manufactured by Johnson & Johnson) was used as a substrate. The substrate was immersed in a solution containing 0.2% by mass of an acrylic acid/N,N-dimethylacrylamide copolymer (molar ratio in copolymerization: 1/9, Mw: 500,000, manufactured by Osaka Organic Chemical Industry Ltd.) in a phosphate buffer solution, which has the pH of 3.0 adjusted with sulfuric acid, followed by heating in an autoclave at 121° C. for 30 minutes. The molded body thus obtained was washed with a phosphate buffer solution while shaking at 250 rpm for 10 seconds. After replacing the phosphate buffer solution by a fresh phosphate buffer solution, the molded body was further heated in the autoclave at 121° C. for 30 minutes. The results obtained by evaluation of the molded body using the above method are shown in Tables 1 to 3.

Example 19

A commercially available silicone hydrogel lens, which has a surface subjected to a plasma treatment and contains silicone as a main component "AIR OPTIX AQUA (registered trademark)" (manufactured by Alcon Japan Ltd.), was used as a substrate. The substrate was immersed in a solution containing 0.2% by mass of an acrylic acid/N,N-dimethylacrylamide copolymer (molar ratio in copolymerization: 1/9, Mw: 800,000, manufactured by Osaka Organic Chemical Industry Ltd.) in a phosphate buffer solution, which has the pH of 2.9 adjusted with sulfuric acid, followed by heating in an autoclave at 121° C. for 30 minutes. The molded body thus obtained was washed with a phosphate buffer solution while shaking at 250 rpm for 10 seconds. After replacing the phosphate buffer solution by a fresh phosphate buffer solution, the molded body was further heated in the autoclave at 121° C. for 30 minutes. The results obtained by evaluation of the molded body using the above method are shown in Tables 1 to 3.

Example 20

A commercially available hydrogel lens containing 2-hydroxyethyl methacrylate obtained by copolymerizing an MPC monomer (2-methacryloyloxyethylphosphorylcholine) as a main component "Proclear 1 Day" (manufactured by CooperVision) was used as a substrate. The substrate was immersed in a solution containing 0.1% by mass of an acrylic acid/vinylpyrrolidone copolymer (molar ratio in copolymerization: 1/4, Mw: 500,000, manufactured by Osaka Organic Chemical Industry Ltd.) in a phosphate buffer solution, which has the pH of 3.8 adjusted with sulfuric acid, followed by heating in an autoclave at 121° C. for 30 minutes. The molded body thus obtained was washed with a phosphate buffer solution while shaking at 250 rpm for 10 seconds. After replacing the phosphate buffer solution by a fresh phosphate buffer solution, the molded body was further heated in the autoclave at 121° C. for 30 minutes. The results obtained by evaluation of the molded body using the above method are shown in Tables 1 to 3.

Example 21

A commercially available hydrogel color lens containing 2-hydroxyethyl methacrylate as a main component "1-Day Acuvue Define Moist (registered trademark)" (manufactured by Johnson & Johnson) was used as a substrate. The substrate was immersed in a solution containing 0.2% by mass of an acrylic acid/N,N-dimethylacrylamide copolymer (molar ratio in copolymerization: 1/9, Mw: 800,000, manufactured by Osaka Organic Chemical Industry Ltd.) in a phosphate buffer solution, which has the pH of 2.7 adjusted with sulfuric acid, followed by heating in an autoclave at 121° C. for 30 minutes. The molded body thus obtained was washed with a phosphate buffer solution while shaking at 250 rpm for 10 seconds. After replacing the phosphate buffer solution by a fresh phosphate buffer solution, the molded body was further heated in the autoclave at 121° C. for 30 minutes. The results obtained by evaluation of the molded body using the above method are shown in Tables 1 to 3.

TABLE 1

|  | Substrate | Moisture content of substrate (%) | Hydrophilic polymer and concentration of solution thereof | Initial pH | pH after heating treatment |
|---|---|---|---|---|---|
| Example 1 | Reference Example 1 | Less than 1% | 0.2% by mass Acrylic acid/N,N-dimethylacrylamide copolymer | 2.6 | 5.0 |
| Example 2 | Reference Example 1 | Less than 1% |  | 2.7 | 4.1 |
| Example 3 | Reference Example 1 | Less than 1% | 0.03% by mass Acrylic acid/N,N-dimethylacrylamide copolymer | 3.1 | 3.8 |
| Example 4 | Reference Example 1 | Less than 1% | 0.2% by mass Acrylic acid/N,N-dimethylacrylamide copolymer | 2.4 | 2.5 |
| Example 5 | Reference Example 1 | Less than 1% |  | 2.4 | 2.7 |
| Example 6 | Reference Example 1 | Less than 1% |  | 2.4 | 3.9 |
| Example 7 | "1-Day Acuvue" | 58 | 0.1% by mass Acrylic acid/vinylpyrrolidone copolymer | 3.1 | 3.7 |
| Example 8 | "1-Day Acuvue" | 58 |  | 4.1 | 4.9 |
| Example 9 | "1-Day Acuvue" | 58 |  | 5.0 | 5.4 |
| Example 10 | "1-Day Acuvue" | 58 |  | 5.7 | 5.9 |
| Example 11 | "1-Day Acuvue" | 58 | 0.2% by mass Acrylic acid/N,N-dimethylacrylamide copolymer | 3.3 | 5.1 |
| Example 12 | "1-Day Acuvue" | 58 |  | 3.0 | 4.7 |
| Example 13 | "1-Day Acuvue" | 58 | 0.2% by mass Acrylic acid/N,N-dimethylacrylamide copolymer | 3.0 | 4.8 |
| Example 14 | "1-Day Acuvue" | 58 | 0.1% by mass Acrylic acid/vinylpyrrolidone copolymer | 4.0 | 4.7 |
| Example 15 | "1-Day Acuvue" | 58 |  | 4.0 | 4.8 |
| Example 16 | "1-Day Acuvue" | 58 | 0.1% by mass Acrylic acid/vinylpyrrolidone copolymer | 4.0 | 4.9 |
| Example 17 | "1-Day Acuvue Trueye" | 46 | 0.2% by mass Acrylic acid/N,N-dimethylacrylamide copolymer | 3.0 | 4.7 |
| Example 18 | "1-Day Acuvue Trueye" | 46 |  | 3.0 | 4.6 |
| Example 19 | "AIR OPTIX AQUA" | 33 | 0.2% by mass Acrylic acid/N,N-dimethylacrylamide copolymer | 2.9 | 4.5 |
| Example 20 | "Proclear 1 Day" | 62 | 0.1% by mass Acrylic acid/vinylpyrrolidone copolymer | 3.8 | 4.2 |
| Example 21 | "1-Day Acuvue Define Moist" | 59 | 0.2% by mass Acrylic acid/N,N-dimethylacrylamide copolymer | 2.7 | 4.2 |

TABLE 2

| | Liquid film retention time (seconds) | Lubricity | Moisture content of device (%) | Number of hydrophilic polymer layers | Results of elemental composition analysis of hydrophilic polymer layer | Moisture content change rate due to fixation of hydrophilic polymer layer (%) | Contact angle (°) | Friction coefficient |
|---|---|---|---|---|---|---|---|---|
| Example 1 | A (45 seconds) | A | 3.2 | Two layers | Coating polymer was separated into two layers (one layer of which was mixed with substrate) | 3.2 | 49.3 | 0.003 |
| Example 2 | A (40 seconds) | A | 3.2 | Two layers | Coating polymer was separated into two layers (one layer of which was mixed with substrate) | 3.2 | 51.9 | 0.006 |
| Example 3 | A (30 seconds) | A | 4.2 | Two layers | Coating polymer was separated into two layers (one layer of which was mixed with substrate) | 4.2 | 53.8 | 0.004 |
| Example 4 | B (19 seconds) | A | 4.0 | Two layers | Coating polymer was separated into two layers (one layer of which was mixed with substrate) | 4.0 | 54.8 | 0.012 |
| Example 5 | B (19 seconds) | A | 5.4 | Two layers | Coating polymer was separated into two layers (one layer of which was mixed with substrate) | 5.4 | 49.1 | 0.018 |
| Example 6 | A (40 seconds) | A | 9.1 | Two layers | Coating polymer was separated into two layers (one layer of which was mixed with substrate) | 9.1 | 42.0 | 0.005 |
| Example 7 | A (120 seconds or more) | A | 59 | Two layers | Coating polymer mixed with substrate and coating polymer alone | 1.0 | 40.7 | 0.009 |
| Example 8 | A (120 seconds or more) | A | 58 | Two layers | Coating polymer mixed with substrate and coating polymer alone | 1.0 | 50.5 | 0.444 |
| Example 9 | A (120 seconds or more) | A | 58 | Two layers | Coating polymer mixed with substrate and coating polymer alone | 0.8 | 51.8 | 0.611 |
| Example 10 | A (120 seconds or more) | C | 58 | Two layers | Coating polymer mixed with substrate and coating polymer alone | 0.8 | 52.4 | 0.615 |
| Example 11 | A (120 seconds or more) | A | 58 | Two layers | Coating polymer mixed with substrate and coating polymer alone | 1.1 | 39.0 | 0.300 |
| Example 12 | A (120 seconds or more) | A | 58 | Two layers | Coating polymer mixed with substrate and coating polymer alone | 0.9 | 39.0 | 0.180 |
| Example 13 | A (120 seconds or more) | A | 58 | Two layers | Coating polymer mixed with substrate and coating polymer alone | 0.8 | 38.3 | 0.050 |
| Example 14 | A (120 seconds or more) | B | 58 | Two layers | Coating polymer mixed with substrate and coating polymer alone | 1.5 | 44.6 | 0.295 |
| Example 15 | A (120 seconds or more) | B | 58 | Two layers | Coating polymer mixed with substrate and coating polymer alone | 1.1 | 54.6 | 0.090 |
| Example 16 | A (120 seconds or more) | A | 58 | Two layers | Coating polymer mixed with substrate and coating polymer alone | 1.0 | 51.4 | 0.160 |
| Example 17 | A (100 seconds) | A | 46.6 | Two layers | Coating polymer mixed with substrate and coating polymer alone | 0.6 | 46.3 | 0.220 |
| Example 18 | A (120 seconds or more) | A | 46.4 | Two layers | Coating polymer mixed with substrate and coating polymer alone | 0.4 | 45.8 | 0.390 |
| Example 19 | A (30 seconds) | A | 35.0 | Two layers | Coating polymer mixed with substrate and coating polymer alone | 2.0 | 52.2 | 0.047 |
| Example 20 | A (120 seconds or more) | A | 62.6 | Two layers | Coating polymer mixed with substrate and coating polymer alone | 0.6 | 50.1 | 0.279 |
| Example 21 | A (120 seconds or more) | A | 59.1 | Two layers | Coating polymer mixed with substrate and coating polymer alone | 0.1 | 52.1 | 0.065 |

TABLE 3

| | Lipid deposition amount | Mucin deposition amount (μg/cm$^2$) | Tensile elastic modulus of substrate (MPa) | Tensile elastic modulus of device (MPa) | Tensile elastic modulus change rate due to fixation of hydrophilic polymer layer (%) | Size of substrate (mm) | Size of device (mm) | Size change rate due to fixation of hydrophilic polymer layer (%) | Film thickness dry state of hydrophilic polymer layer (nm) | Film thickness frozen state of hydrophilic polymer layer (nm) |
|---|---|---|---|---|---|---|---|---|---|---|
| Example 1 | Not deposited | 8.56 | 0.53 | 0.49 | −6.7 | 14.00 | 14.01 | 0.1 | 10 to 17 | 30 to 45 |
| Example 2 | Not deposited | 6.18 | 0.53 | 0.49 | −6.7 | 14.00 | 14.01 | 0.1 | 11 to 16 | 32 to 48 |
| Example 3 | Not deposited | 9.50 | 0.53 | 0.49 | −6.7 | 14.00 | 14.01 | 0.1 | 5 to 12 | 30 to 43 |
| Example 4 | Not deposited | 1.57 | 0.53 | 0.49 | −6.7 | 14.00 | 14.01 | 0.1 | 15 to 20 | 34 to 46 |
| Example 5 | Not deposited | 1.53 | 0.53 | 0.49 | −6.7 | 14.00 | 14.01 | 0.1 | 10 to 20 | 29 to 41 |

TABLE 3-continued

| | Lipid deposition amount | Mucin deposition amount (μg/cm²) | Tensile elastic modulus of substrate (MPa) | Tensile elastic modulus of device (MPa) | Tensile elastic modulus change rate due to fixation of hydrophilic polymer layer (%) | Size of substrate (mm) | Size of device (mm) | Size change rate due to fixation of hydrophilic polymer layer (%) | Film thickness dry state of hydrophilic polymer layer (nm) | Film thickness frozen state of hydrophilic polymer layer (nm) |
|---|---|---|---|---|---|---|---|---|---|---|
| Example 6 | Not deposited | 5.70 | 0.53 | 0.49 | −6.7 | 14.00 | 14.01 | 0.1 | 15 to 25 | 28 to 39 |
| Example 7 | Not deposited | 3.25 | 0.30 | 0.26 | −13.1 | 14.20 | 13.90 | −2.1 | 15 to 20 | 40 to 53 |
| Example 8 | Not deposited | 1.94 | 0.30 | 0.26 | −13.1 | 14.20 | 13.90 | −2.1 | 10 to 18 | 41 to 51 |
| Example 9 | Not deposited | 2.68 | 0.30 | 0.26 | −13.1 | 14.20 | 13.90 | −2.1 | 8 to 15 | 30 to 40 |
| Example 10 | Not deposited | 2.86 | 0.30 | 0.26 | −13.1 | 14.20 | 13.90 | −2.1 | 5 to 10 | 29 to 44 |
| Example 11 | Not deposited | 2.78 | 0.30 | 0.28 | −6.8 | 14.20 | 13.95 | −1.8 | 22 to 35 | 42 to 56 |
| Example 12 | Not deposited | 3.65 | 0.30 | 0.28 | −6.8 | 14.20 | 13.95 | −1.8 | 20 to 35 | 45 to 59 |
| Example 13 | Not deposited | 9.00 | 0.30 | 0.28 | −6.8 | 14.20 | 13.95 | −1.8 | 22 to 40 | 40 to 50 |
| Example 14 | Not deposited | 1.53 | 0.30 | 0.26 | −13.1 | 14.20 | 13.90 | −2.1 | 22 to 37 | 40 to 55 |
| Example 15 | Not deposited | 3.48 | 0.30 | 0.26 | −13.1 | 14.20 | 13.90 | −2.1 | 20 to 40 | 35 to 45 |
| Example 16 | Not deposited | 3.26 | 0.30 | 0.26 | −13.1 | 14.20 | 13.90 | −2.1 | 20 to 35 | 40 to 51 |
| Example 17 | Not deposited | 2.85 | 0.70 | 0.71 | 0.40 | 14.20 | 14.23 | 0.2 | 10 to 17 | 70 to 98 |
| Example 18 | Not deposited | 3.05 | 0.70 | 0.71 | 0.40 | 14.20 | 14.23 | 0.2 | 10 to 20 | 80 to 95 |
| Example 19 | Not deposited | 4.00 | 1.0 | 1.1 | 2.7 | 14.15 | 14.20 | 0.4 | 10 to 25 | 40 to 50 |
| Example 20 | Not deposited | 2.45 | 0.41 | 0.35 | −13.5 | 14.15 | 14.20 | 0.4 | 11 to 23 | 50 to 65 |
| Example 21 | Not deposited | 3.00 | 0.26 | 0.25 | −5.4 | 14.05 | 14.05 | 0 | 10 to 28 | 30 to 45 |

Comparative Example 1

The molded body obtained in Reference Example 1 was used as a substrate. The substrate was immersed in a solution containing 0.2% by mass of an acrylic acid/N,N-dimethylacrylamide copolymer (molar ratio in copolymerization: 1/9, Mw: 800,000, manufactured by Osaka Organic Chemical Industry Ltd.) in a phosphate buffer solution (pH 6.8), followed by heating in an autoclave at 121° C. for 30 minutes. The molded body thus obtained was washed with a phosphate buffer solution while shaking at 250 rpm for 10 seconds. After replacing the phosphate buffer solution by a fresh phosphate buffer solution, the molded body was further heated in the autoclave at 121° C. for 30 minutes. The results obtained by evaluation of the molded body using the above method are shown in Tables 4 to 6.

Comparative Example 2

The molded body obtained in Reference Example 1 was used as a substrate. The substrate was immersed in a solution in which the pH of a phosphate buffer was adjusted to 2.7 with sulfuric acid, followed by heating in an autoclave at 121° C. for 30 minutes. The molded body thus obtained was washed with a phosphate buffer solution while shaking at 250 rpm for 10 seconds. After replacing the phosphate buffer solution by a fresh phosphate buffer solution, the molded body was further heated in the autoclave at 121° C. for 30 minutes. The results obtained by evaluation of the molded body using the above method are shown in Tables 4 to 6.

Comparative Example 3

The molded body obtained in Reference Example 1 was used as a substrate. The substrate was immersed in a solution containing 0.20 by mass of an acrylic acid/N,N-dimethylacrylamide copolymer (molar ratio in copolymerization: 1/9, Mw: 800,000, manufactured by Osaka Organic Chemical Industry Ltd.) in a phosphate buffer solution (pH 6.8) and then left to stand at room temperature (23° C.) overnight. The molded body thus obtained was washed with a phosphate buffer solution while shaking at 250 rpm for 10 seconds. After replacing the phosphate buffer solution by a fresh phosphate buffer solution, the molded body was further heated in the autoclave at 121° C. for 30 minutes. The results obtained by evaluation of the molded body using the above method are shown in Tables 4 to 6.

Comparative Example 4

A commercially available hydrogel lens containing 2-hydroxyethyl methacrylate as a main component "1-Day Acuvue (registered trademark)" (manufactured by Johnson & Johnson) was used as a substrate. The substrate was immersed in a solution containing 0.2% by mass of an acrylic acid/N,N-dimethylacrylamide copolymer (molar ratio in copolymerization: 1/9, Mw: 800,000, manufactured by Osaka Organic Chemical Industry Ltd.) in a phosphate buffer solution (pH 6.8) and then left to stand at room temperature (23° C.) overnight. The molded body thus obtained was washed with a phosphate buffer solution while shaking at 250 rpm for 10 seconds. After replacing the phosphate buffer solution by a fresh phosphate buffer solution, the molded body was further heated in the autoclave at 121° C. for 30 minutes. The results obtained by evaluation of the molded body using the above method are shown in Tables 4 to 6.

Comparative Example 5

The molded body obtained in Reference Example 1 was used as a substrate. The substrate was immersed in a solution containing 0.1% by mass of polyacrylic acid "Sokalan (registered trademark) PA110S" (Mw: 250,000, manufactured by BASF) in a phosphate buffer (pH 5.3), followed by heating in an autoclave at 121° C. for 30 minutes. The molded body thus obtained was washed with a phosphate buffer solution while shaking at 250 rpm for 10 seconds. After replacing the phosphate buffer solution by a fresh phosphate buffer solution, the molded body was further heated in the autoclave at 121° C. for 30 minutes. The results obtained by evaluation of the molded body using the above method are shown in Tables 4 to 6.

Comparative Example 6

The molded body obtained in Reference Example 1 was used as a substrate. The substrate was immersed in a solution containing 0.2% by mass of polydimethylacrylamide (Mw: 360,000, manufactured by Osaka Organic Chemical Industry Ltd.) in a phosphate buffer, which has the pH of 2.5 adjusted with sulfuric acid, followed by heating in an autoclave at 121° C. for 30 minutes. The molded body thus obtained was washed with a phosphate buffer solution while shaking at 250 rpm for 10 seconds. After replacing the phosphate buffer solution by a fresh phosphate buffer solution, the molded body was further heated in the autoclave at 121° C. for 30 minutes. The results obtained by evaluation of the molded body using the above method are shown in Tables 4 to 6.

Comparative Example 7

The molded body obtained in Reference Example 1 was used as a substrate. The substrate was immersed in a solution containing 0.2% by mass of polyvinylpyrrolidone K-90 (Mw: 360,000, manufactured by Tokyo Chemical Industry Co., Ltd.) in a phosphate buffer, which has the pH of 2.5 adjusted with sulfuric acid, followed by heating in an autoclave at 121° C. for 30 minutes. The molded body thus obtained was washed with a phosphate buffer solution while shaking at 250 rpm for 10 seconds. After replacing the phosphate buffer solution by a fresh phosphate buffer solution, the molded body was further heated in the autoclave at 121° C. for 30 minutes. The results obtained by evaluation of the molded body using the above method are shown in Tables 4 to 6.

Comparative Example 8

The molded body obtained in Reference Example 1 was used as a substrate. The substrate was immersed in a solution containing 0.2% by mass of Polyethylene Glycol 200 (Mw: 180 to 200, manufactured by Wako Pure Chemical Industries, Ltd.) in a phosphate buffer, which has the pH of 2.5 adjusted with sulfuric acid, followed by heating in an autoclave at 121° C. for 30 minutes. The molded body thus obtained was washed with a phosphate buffer solution while shaking at 250 rpm for 10 seconds. After replacing the phosphate buffer solution by a fresh phosphate buffer solution, the molded body was further heated in the autoclave at 121° C. for 30 minutes. The results obtained by evaluation of the molded body using the above method are shown in Tables 4 to 6.

Comparative Example 9

The molded body obtained in Reference Example 1 was used as a substrate. The substrate was immersed in a solution containing 0.2% by mass of poly-N-vinylacetamide "GE-191-103" (Mw: 1,000,000, manufactured by Showa Denko K.K.) in a phosphate buffer, which has the pH of 2.5 adjusted with sulfuric acid, followed by heating in an autoclave at 121° C. for 30 minutes. The molded body thus obtained was washed with a phosphate buffer solution while shaking at 250 rpm for 10 seconds. After replacing the phosphate buffer solution by a fresh phosphate buffer solution, the molded body was further heated in the autoclave at 121° C. for 30 minutes. The results obtained by evaluation of the molded body using the above method are shown in Tables 4 to 6.

Comparative Example 10

The molded body obtained in Reference Example 1 was used as a substrate. After making a trial of immersing the substrate in a solution containing 0.1% by mass of polyvinyl alcohol (Mw: 31,000 to 50,000, manufactured by SIGMA-ALDRICH) in a phosphate buffer, a precipitate was formed in the solution due to inferior solubility of polyvinyl alcohol, thus failing to perform coating.

Comparative Example 11

The molded body obtained in Reference Example 1 was used as a substrate. The substrate was immersed in a solution containing 0.2% by mass of "Methyl Cellulose 400" (Mw: 84,000, manufactured by Wako Pure Chemical Industries, Ltd.) in a phosphate buffer, which has the pH of 2.5 adjusted with sulfuric acid, followed by heating in an autoclave at 121° C. for 30 minutes. The molded body thus obtained was washed with a phosphate buffer solution while shaking at 250 rpm for 10 seconds. After replacing the phosphate buffer solution by a fresh phosphate buffer solution, the molded body was further heated in the autoclave at 121° C. for 30 minutes. The results obtained by evaluation of the molded body using the above method are shown in Tables 4 to 6.

Comparative Example 12

The molded body obtained in Reference Example 1 was used as a substrate. The substrate was immersed in a solution containing 0.2% by mass of Poloxamer 407 (Mw: 11,500, manufactured by BASF) in a phosphate buffer, which has the pH of 2.5 adjusted with sulfuric acid, followed by heating in an autoclave at 121° C. for 30 minutes. The molded body thus obtained was washed with a phosphate buffer solution while shaking at 250 rpm for 10 seconds. After replacing the phosphate buffer solution by a fresh phosphate buffer solution, the molded body was further heated in the autoclave at 121° C. for 30 minutes. The results obtained by evaluation of the molded body using the above method are shown in Tables 4 to 6.

Comparative Example 13

The molded body obtained in Reference Example 1 was used as a substrate. The substrate was immersed in a solution containing 0.2% by mass of sodium alginate (manufactured by SHOWA CHEMICAL CO., LTD.) in a phosphate buffer, which has the pH of 2.5 adjusted with sulfuric acid, followed by heating in an autoclave at 121° C. for 30 minutes. The molded body thus obtained was washed with a phosphate buffer solution while shaking at 250 rpm for 10 seconds. After replacing the phosphate buffer solution by a fresh phosphate buffer solution, the molded body was further heated in the autoclave at 121° C. for 30 minutes. The results obtained by evaluation of the molded body using the above method are shown in Tables 4 to 6.

Comparative Example 14

The molded body obtained in Reference Example 1 was used as a substrate. The substrate was immersed in a solution containing 0.05% by mass of poly-2-acrylamido-2-methyl-propanesulfonic acid (Mw: 200,000, manufactured by oneself) in a phosphate buffer (pH 6.8), followed by heating in an autoclave at 121° C. for 30 minutes. The molded body thus obtained was washed with a phosphate buffer solution while shaking at 250 rpm for 10 seconds. After replacing the phosphate buffer solution by a fresh phosphate buffer solution, the molded body was further heated in the autoclave at 121° C. for 30 minutes. The results obtained by evaluation of the molded body using the above method are shown in Tables 4 to 6.

Comparative Example 15

The molded body obtained in Reference Example 1 was used as a substrate. The substrate was immersed in a solution containing 0.05% by mass of poly-2-acrylamido-2-methyl-propanesulfonic acid/N,N-dimethylacrylamide copolymer (molar ratio in copolymerization: 1/9, Mw: 200,000, manufactured by oneself) in a phosphate buffer (pH 6.8), followed by heating in an autoclave at 121° C. for 30 minutes. The molded body thus obtained was washed with a phosphate buffer solution while shaking at 250 rpm for 10 seconds. After replacing the phosphate buffer solution by a fresh phosphate buffer solution, the molded body was further heated in the autoclave at 121° C. for 30 minutes. The results obtained by evaluation of the molded body using the above method are shown in Tables 4 to 6.

Comparative Example 16

The molded body obtained in Reference Example 1 was used as a substrate. The substrate was immersed in a solution containing 0.2% by mass of a polyvinyl acetate/polyvinylpyrrolidone copolymer "PVA-6450" (Mw: 50,000, manufactured by Osaka Organic Chemical Industry Ltd.) in a phosphate buffer solution, which has the pH of 2.5 adjusted with sulfuric acid, followed by heating in an autoclave at 121° C. for 30 minutes. The molded body thus obtained was washed with a phosphate buffer solution while shaking at 250 rpm for 10 seconds. After replacing the phosphate buffer solution by a fresh phosphate buffer solution, the molded body was further heated in the autoclave at 121° C. for 30 minutes. The results obtained by evaluation of the molded body using the above method are shown in Tables 4 to 6.

Comparative Example 17

A commercially available hydrogel lens containing 2-hydroxyethyl methacrylate as a main component "1-Day Acuvue (registered trademark)" (manufactured by Johnson & Johnson) was used as a substrate. The substrate was immersed in a solution containing 0.2% by mass of a polyvinyl acetate/polyvinylpyrrolidone copolymer "PVA-6450" (Mw: 50,000, manufactured by Osaka Organic Chemical Industry Ltd.) in a phosphate buffer solution, which has the pH of 2.5 adjusted with sulfuric acid, followed by heating in an autoclave at 121° C. for 30 minutes. The molded body thus obtained was washed with a phosphate buffer solution while shaking at 250 rpm for 10 seconds. After replacing the phosphate buffer solution by a fresh phosphate buffer solution, the molded body was further heated in the autoclave at 121° C. for 30 minutes. The results obtained by evaluation of the molded body using the above method are shown in Tables 4 to 6.

Comparative Example 18

A commercially available silicone hydrogel lens containing polyvinylpyrrolidone and silicone as main components "1-Day Acuvue TruEye (registered trademark)" (manufactured by Johnson & Johnson) was used as a substrate. The substrate was immersed in a solution containing 0.2% by mass of a polyvinyl acetate/polyvinylpyrrolidone copolymer "PVA-6450" (Mw: 50,000, manufactured by Osaka Organic Chemical Industry Ltd.) in a phosphate buffer solution, which has the pH of 2.5 adjusted with sulfuric acid, followed by heating in an autoclave at 121° C. for 30 minutes. The molded body thus obtained was washed with a phosphate buffer solution while shaking at 250 rpm for 10 seconds. After replacing the phosphate buffer solution by a fresh phosphate buffer solution, the molded body was further heated in the autoclave at 121° C. for 30 minutes. The results obtained by evaluation of the molded body using the above method are shown in Tables 4 to 6.

Comparative Example 19

A commercially available hydrogel lens containing 2-hydroxyethyl methacrylate as a main component "1-Day Acuvue (registered trademark)" (manufactured by Johnson & Johnson) was used as a substrate. The substrate was immersed in a solution containing 0.2% by mass of poly-N-vinylacetamide "GE-191-103" (Mw: 1,000,000, manufactured by Showa Denko K.K.) in a phosphate buffer solution, which has the pH of 2.5 adjusted with sulfuric acid, followed by heating in an autoclave at 121° C. for 30 minutes. The molded body thus obtained was washed with a phosphate buffer solution while shaking at 250 rpm for 10 seconds. After replacing the phosphate buffer solution by a fresh phosphate buffer solution, the molded body was further heated in the autoclave at 121° C. for 30 minutes. The results obtained by evaluation of the molded body using the above method are shown in Tables 4 to 6.

Comparative Example 20

A commercially available silicone hydrogel lens containing polyvinylpyrrolidone and silicone as main components "1-Day Acuvue TruEye (registered trademark)" (manufactured by Johnson & Johnson) was used as a substrate. The substrate was immersed in a solution containing 0.2% by mass of poly-N-vinylacetamide "GE-191-103" (Mw: 1,000,000, manufactured by Showa Denko K.K.) in a phosphate buffer solution, which has the pH of 2.5 adjusted with sulfuric acid, followed by heating in an autoclave at 121° C. for 30 minutes. The molded body thus obtained was washed with a phosphate buffer solution while shaking at 250 rpm for 10 seconds. After replacing the phosphate buffer solution by a fresh phosphate buffer solution, the molded body was further heated in the autoclave at 121° C. for 30 minutes. The results obtained by evaluation of the molded body using the above method are shown in Tables 4 to 6.

Comparative Example 21

A commercially available hydrogel lens containing 2-hydroxyethyl methacrylate as a main component "1-Day Acuvue (registered trademark)" (manufactured by Johnson & Johnson) was used as a substrate. The substrate was immersed in a solution containing 0.2% by mass of sodium alginate (manufactured by SHOWA CHEMICAL CO., LTD.) in a phosphate buffer solution, which has the pH of 2.5 adjusted with sulfuric acid, followed by heating in an autoclave at 121° C. for 30 minutes. The molded body thus obtained was washed with a phosphate buffer solution while shaking at 250 rpm for 10 seconds. After replacing the phosphate buffer solution by a fresh phosphate buffer solution, the molded body was further heated in the autoclave at 121° C. for 30 minutes. The results obtained by evaluation of the molded body using the above method are shown in Tables 4 to 6.

TABLE 4

| | Substrate | Moisture content of substrate (%) | Hydrophilic polymer and concentration of solution thereof | Initial pH | pH after heating treatment |
|---|---|---|---|---|---|
| Comparative Example 1 | Reference Example 1 | Less than 1% | 0.2% by mass Acrylic acid/N,N-dimethylacrylamide copolymer | 6.8 | 6.9 |
| Comparative Example 2 | Reference Example 1 | Less than 1% | Containing no polymer | 2.7 | 2.8 |
| Comparative Example 3 | Reference Example 1 | Less than 1% | 0.2% by mass Acrylic acid/N,N-dimethylacrylamide copolymer | 6.8 | 6.8 |
| Comparative Example 4 | "1-Day Acuvue" | 58 | 0.2% by mass Acrylic acid/N,N-dimethylacrylamide copolymer | 6.8 | 6.9 |
| Comparative Example 5 | Reference Example 1 | Less than 1% | 0.1% by mass Polyacrylic acid | 5.3 | 5.3 |
| Comparative Example 6 | Reference Example 1 | Less than 1% | 0.2% by mass Polydimethylacrylamide | 2.5 | 2.5 |
| Comparative Example 7 | Reference Example 1 | Less than 1% | 0.2% by mass Polyvinylpyrrolidone | 2.5 | 2.5 |
| Comparative Example 8 | Reference Example 1 | Less than 1% | 0.2% by mass Polyethylene glycol 200 | 2.5 | 2.5 |
| Comparative Example 9 | Reference Example 1 | Less than 1% | 0.2% by mass Poly-N-vinylacetamide | 2.5 | 2.5 |
| Comparative Example 10 | Reference Example 1 | Less than 1% | 0.1% by mass Polyvinyl alcohol | *Impossible to perform coating due to inferior solubility | *Impossible to perform coating due to inferior solubility |
| Comparative Example 11 | Reference Example 1 | Less than 1% | 0.2% by mass Methyl Cellulose 400 | 2.5 | 2.5 |
| Comparative Example 12 | Reference Example 1 | Less than 1% | 0.2% by mass Poloxamer 407 | 2.5 | 2.5 |
| Comparative Example 13 | Reference Example 1 | Less than 1% | 0.2% by mass Sodium alginate | 2.5 | 2.5 |
| Comparative Example 14 | Reference Example 1 | Less than 1% | 0.05% by mass Poly-2-acrylamido-2-methylpropanesulfonic acid | 6.8 | 6.9 |
| Comparative Example 15 | Reference Example 1 | Less than 1% | 0.05% by mas 2-Acrylamido-2-methylpropanesulfonic acid/N,Ndimethylacrylamide copolymer | 6.8 | 6.9 |
| Comparative Example 16 | Reference Example 1 | Less than 1% | 0.2% by mass Vinylpyrrolidone/vinyl acetate copolymer | 2.5 | 2.4 |
| Comparative Example 17 | "1-Day Acuvue" | 58 | 0.2% by mass Vinylpyrrolidone/vinyl acetate copolymer | 2.5 | 2.6 |
| Comparative Example 18 | "1-Day Acuvue Trueye" | 46 | 0.2% by mass Vinylpyrrolidone/vinyl acetate copolymer | 2.5 | 2.6 |
| Comparative Example 19 | "1-Day Acuvue" | 58 | 0.2% by mass Poly-N-vinylacetamide | 2.5 | 2.5 |
| Comparative Example 20 | "1-Day Acuvue Trueye" | 46 | 0.2% by mass Poly-N-vinylacetamide | 2.5 | 2.5 |
| Comparative Example 21 | "1-Day Acuvue" | 58 | 0.2% by mass Sodium alginate | 2.5 | 2.6 |

TABLE 5

| | Liquid film retention time (seconds) | Lubricity | Moisture content of device (%) | Number of hydrophilic polymer layers | Moisture content change rate due to fixation of hydrophilic polymer layer (%) | Contact angle (°) | Friction coefficient |
|---|---|---|---|---|---|---|---|
| Comparative Example 1 | E (0 second) | D | Less than 1% | Impossible to confirm layer | 0 | 83.0 | 0.850 |
| Comparative Example 2 | E (0 second) | E | Less than 1% | Impossible to confirm layer | None | 81.9 | 0.852 |
| Comparative Example 3 | E (0 second) | E | Less than 1% | Impossible to confirm layer | 0 | 80.0 | 0.852 |
| Comparative Example 4 | A (20 seconds) | E | 58% | Impossible to confirm layer | 0 | 54.0 | 0.677 |
| Comparative Example 5 | E (0 second) | E | Less than 1% | Impossible to confirm layer | 0 | 79.0 | 0.849 |
| Comparative Example 6 | E (0 second) | E | Less than 1% | Impossible to confirm layer | 0 | 82.0 | 0.840 |
| Comparative Example 7 | E (0 second) | E | Less than 1% | Impossible to confirm layer | 0 | 80.9 | 0.839 |
| Comparative Example 8 | E (0 second) | E | Less than 1% | Impossible to confirm layer | 0 | 81.9 | 0.850 |
| Comparative Example 9 | E (0 second) | E | Less than 1% | Impossible to confirm layer | 0 | 83.5 | 0.830 |
| Comparative Example 10 | *Impossible to perform coating due to inferior solubility | *Impossible to perform coating due to inferior solubility | *Impossible to perform coating due to inferior solubility | *Impossible to perform coating due to inferior solubility | *Impossible to perform coating due to inferior solubility | *Impossible to perform coating due to inferior solubility | *Impossible to perform coating due to inferior solubility |
| Comparative Example 11 | E (0 second) | E | Less than 1% | Impossible to confirm layer | 0 | 83.0 | 0.860 |
| Comparative Example 12 | E (0 second) | E | Less than 1% | Impossible to confirm layer | 0 | 82.9 | 0.841 |
| Comparative Example 13 | E (0 second) | E | Less than 1% | Impossible to confirm layer | 0 | 80.1 | 0.852 |
| Comparative Example 14 | E (0 second) | E | Less than 1% | Impossible to confirm layer | 0 | 78.0 | 0.854 |
| Comparative Example 15 | E (0 second) | E | Less than 1% | Impossible to confirm layer | 0 | 81.7 | 0.830 |
| Comparative Example 16 | E (0 second) | E | Less than 1% | Impossible to confirm layer | 0 | 80.0 | 0.820 |
| Comparative Example 17 | A (20 seconds) | D | 58 | Impossible to confirm layer | 0 | 53.5 | 0.450 |
| Comparative Example 18 | C (12 seconds) | C | 46 | Impossible to confirm layer | 0 | 48.0 | 0.130 |
| Comparative Example 19 | C (10 seconds) | D | 58 | Impossible to confirm layer | 0 | 54.0 | 0.470 |
| Comparative Example 20 | C (12 seconds) | C | 46 | Impossible to confirm layer | 0 | 47.0 | 0.120 |
| Comparative Example 21 | C (10 seconds) | D | 58 | Impossible to confirm layer | 0 | 53.9 | 0.419 |

TABLE 6

| | Lipid deposition amount | Mucin deposition amount (μg/cm$^2$) | Tensile elastic modulus of substrate (MPa) | Tensile elastic modulus of device (MPa) | Tensile elastic modulus change rate due to fixation of hydrophilic polymer layer (%) | Size of substrate (mm) | Size of device (mm) | Size change rate due to fixation of hydrophilic polymer layer (%) | Film thickness dried state of hydrophilic polymer layer (nm) | Film thickness frozen state of hydrophilic polymer layer (nm) |
|---|---|---|---|---|---|---|---|---|---|---|
| Comparative Example 1 | Deposited on entire surface | 3.20 | 0.53 | 0.49 | −6.8 | 14.00 | 14.01 | 0.1 | 0 | 0 |
| Comparative Example 2 | Deposited on entire surface | 3.00 | 0.53 | None | None | 14.00 | None | None | 0 | 0 |
| Comparative Example 3 | Deposited on entire surface | 2.95 | 0.53 | 0.49 | −6.8 | 14.00 | 14.01 | 0.1 | 0 | 0 |
| Comparative Example 4 | Not deposited | 2.88 | 0.30 | 0.28 | −6.8 | 14.20 | 14.05 | −1.1 | 0 | 0 |
| Comparative Example 5 | Deposited on entire surface | 3.35 | 0.53 | 0.49 | −6.8 | 14.00 | 14.00 | 0.0 | 0 | 0 |
| Comparative Example 6 | Deposited on entire surface | 3.00 | 0.53 | 0.49 | −6.8 | 14.00 | 14.00 | 0.0 | 0 | 0 |

TABLE 6-continued

| | Lipid deposition amount | Mucin deposition amount (μg/cm²) | Tensile elastic modulus of substrate (MPa) | Tensile elastic modulus of device (MPa) | Tensile elastic modulus change rate due to fixation of hydrophilic polymer layer (%) | Size of substrate (mm) | Size of device (mm) | Size change rate due to fixation of hydrophilic polymer layer (%) | Film thickness dried state of hydrophilic polymer layer (nm) | Film thickness frozen state of hydrophilic polymer layer (nm) |
|---|---|---|---|---|---|---|---|---|---|---|
| Comparative Example 7 | Deposited on entire surface | 3.10 | 0.53 | 0.49 | −6.8 | 14.00 | 14.00 | 0.0 | 0 | 0 |
| Comparative Example 8 | Deposited on entire surface | Deposited on entire surface 2.98 | 0.53 | 0.49 | −6.8 | 14.00 | 14.00 | 0.0 | 0 | 0 |
| Comparative Example 9 | Deposited on entire surface | 3.40 | 0.53 | 0.49 | −6.8 | 14.00 | 14.00 | 0.0 | 0 | 0 |
| Comparative Example 10 | *Impossible to perform coating due to inferior solubility | *Impossible to perform coating due to inferior solubility | 0.53 | *Impossible to perform coating due to inferior solubility | *Impossible to perform coating due to inferior solubility | 14.00 | *Impossible to perform coating due to inferior solubility | *Impossible to perform coating due to inferior solubility | *Impossible to perform coating due to inferior solubility | *Impossible to perform coating due to inferior solubility |
| Comparative Example 11 | Deposited on entire surface | 3.29 | 0.53 | 0.49 | −6.8 | 14.00 | 14.00 | 0.0 | 0 | 0 |
| Comparative Example 12 | Deposited on entire surface | 2.99 | 0.53 | 0.49 | −6.8 | 14.00 | 14.00 | 0.0 | 0 | 0 |
| Comparative Example 13 | Deposited on entire surface | 3.04 | 0.53 | 0.49 | −6.8 | 14.00 | 14.00 | 0.0 | 0 | 0 |
| Comparative Example 14 | Deposited on entire surface | 3.00 | 0.53 | 0.49 | −6.8 | 14.00 | 14.00 | 0.0 | 0 | 0 |
| Comparative Example 15 | Deposited on entire surface | 3.30 | 0.53 | 0.49 | −6.8 | 14.00 | 14.00 | 0.0 | 0 | 0 |
| Comparative Example 16 | Deposited on entire surface | 2.91 | 0.42 | 0.49 | 15.1 | 14.00 | 14.00 | 0.0 | 0 | 0 |
| Comparative Example 17 | Not deposited | 2.25 | 0.30 | 0.28 | −7.7 | 14.20 | 13.90 | −2.1 | 0 | 0 |
| Comparative Example 18 | Deposited in area accounting for ⅓ of entire area | 1.00 | 0.70 | 0.60 | −15.3 | 14.20 | 14.30 | 0.7 | 0 | 0 |
| Comparative Example 19 | Not deposited | 2.30 | 0.30 | 0.29 | −4.4 | 14.20 | 14.10 | −0.7 | 0 | 0 |
| Comparative Example 20 | Deposited in area accounting for ⅓ of entire area | 1.10 | 0.70 | 0.71 | 0.40 | 14.20 | 14.20 | 0.0 | 0 | 0 |
| Comparative Example 21 | Not deposited | 2.20 | 0.30 | 0.29 | −4.4 | 14.20 | 14.10 | −0.7 | 0 | 0 |

Comparative Example 22

A commercially available silicone hydrogel lens containing polyvinylpyrrolidone and silicone as main components "1-Day Acuvue TruEye (registered trademark)" (manufactured by Johnson & Johnson) was used as a substrate. The substrate was immersed in a solution containing 0.2% by mass of sodium alginate (manufactured by SHOWA CHEMICAL CO., LTD.) in a phosphate buffer solution, which has the pH of 2.5 adjusted with sulfuric acid, followed by heating in an autoclave at 121° C. for 30 minutes. The molded body thus obtained was washed with a phosphate buffer solution while shaking at 250 rpm for 10 seconds. After replacing the phosphate buffer solution by a fresh phosphate buffer solution, the molded body was further heated in the autoclave at 121° C. for 30 minutes. The results obtained by evaluation of the molded body using the above method are shown in Tables 7 to 9.

Comparative Example 23

A commercially available hydrogel lens containing 2-hydroxyethyl methacrylate as a main component "1-Day Acuvue (registered trademark)" (manufactured by Johnson & Johnson) was used as a substrate. The substrate was immersed in a solution containing 0.2% by mass of Poloxamer 407 (Mw: 11,500, manufactured by BASF) in a phosphate buffer solution, which has the pH of 2.5 adjusted with sulfuric acid, followed by heating in an autoclave at 121° C. for 30 minutes. The molded body thus obtained was washed with a phosphate buffer solution while shaking at 250 rpm for 10 seconds. After replacing the phosphate buffer solution by a fresh phosphate buffer solution, the molded body was further heated in the autoclave at 121° C. for 30 minutes. The results obtained by evaluation of the molded body using the above method are shown in Tables 7 to 9.

Comparative Example 24

A commercially available silicone hydrogel lens containing polyvinylpyrrolidone and silicone as main components "1-Day Acuvue TruEye (registered trademark)" (manufactured by Johnson & Johnson) was used as a substrate. The substrate was immersed in a solution containing 0.2% by mass of Poloxamer 407 (Mw: 11,500, manufactured by BASF Japan) in a phosphate buffer solution, which has the pH of 2.5 adjusted with sulfuric acid, followed by heating in an autoclave at 121° C. for 30 minutes. The molded body thus obtained was washed with a phosphate buffer solution while shaking at 250 rpm for 10 seconds. After replacing the phosphate buffer solution by a fresh phosphate buffer solution, the molded body was further heated in the autoclave at 121° C. for 30 minutes. The results obtained by evaluation of the molded body using the above method are shown in Tables 7 to 9.

Comparative Example 25

A commercially available hydrogel lens containing 2-hydroxyethyl methacrylate as a main component "1-Day Acuvue (registered trademark)" (manufactured by Johnson & Johnson) was used as a substrate. The substrate was immersed in a solution containing 0.05% by mass of poly-2-acrylamido-2-methylpropanesulfonic acid (Mw: 200,000, manufactured by oneself) in a phosphate buffer (pH 6.8), followed by heating in an autoclave at 121° C. for 30 minutes. The molded body thus obtained was washed with a phosphate buffer solution while shaking at 250 rpm for 10 seconds. After replacing the phosphate buffer solution by a fresh phosphate buffer solution, the molded body was further heated in the autoclave at 121° C. for 30 minutes. The results obtained by evaluation of the molded body using the above method are shown in Tables 7 to 9.

Comparative Example 26

A commercially available silicone hydrogel lens containing polyvinylpyrrolidone and silicone as main components "1-Day Acuvue TruEye (registered trademark)" (manufactured by Johnson & Johnson) was used as a substrate. The substrate was immersed in a solution containing 0.05% by mass of poly-2-acrylamido-2-methylpropanesulfonic acid (Mw: 200,000, manufactured by oneself) in a phosphate buffer (pH 6.8), followed by heating in an autoclave at 121° C. for 30 minutes. The molded body thus obtained was washed with a phosphate buffer solution while shaking at 250 rpm for 10 seconds. After replacing the phosphate buffer solution by a fresh phosphate buffer solution, the molded body was further heated in the autoclave at 121° C. for 30 minutes. The results obtained by evaluation of the molded body using the above method are shown in Tables 7 to 9.

Comparative Example 27

A commercially available hydrogel lens containing 2-hydroxyethyl methacrylate as a main component "1-Day Acuvue (registered trademark)" (manufactured by Johnson & Johnson) was used as a substrate. The substrate was immersed in a solution containing 0.05% by mass of a poly-2-acrylamido-2-methylpropanesulfonic acid/N,N-dimethylacrylamide copolymer (molar ratio in copolymerization: 1/9, Mw: 200,000, manufactured by oneself) in a phosphate buffer (pH 6.8), followed by heating in an autoclave at 121° C. for 30 minutes. The molded body thus obtained was washed with a phosphate buffer solution while shaking at 250 rpm for 10 seconds. After replacing the phosphate buffer solution by a fresh phosphate buffer solution, the molded body was further heated in the autoclave at 121° C. for 30 minutes. The results obtained by evaluation of the molded body using the above method are shown in Tables 7 to 9.

Comparative Example 28

A commercially available silicone hydrogel lens containing polyvinylpyrrolidone and silicone as main components "1-Day Acuvue TruEye (registered trademark)" (manufactured by Johnson & Johnson) was used as a substrate. The substrate was immersed in a solution containing 0.05% by mass of a poly-2-acrylamido-2-methylpropanesulfonic acid/N,N-dimethylacrylamide copolymer (molar ratio in copolymerization: 1/9, Mw: 200,000, manufactured by oneself) in a phosphate buffer (pH 6.8), followed by heating in an autoclave at 121° C. for 30 minutes. The molded body thus obtained was washed with a phosphate buffer solution while shaking at 250 rpm for 10 seconds. After replacing the phosphate buffer solution by a fresh phosphate buffer solution, the molded body was further heated in the autoclave at 121° C. for 30 minutes. The results obtained by evaluation of the molded body using the above method are shown in Tables 7 to 9.

Comparative Example 29

The molded body obtained in Reference Example 1 was used as a substrate. The substrate was immersed in an aqueous solution containing 0.1% by mass of an acrylic acid/vinylpyrrolidone copolymer (molar ratio in copolymerization: 1/9, Mw: 400,000, manufactured by Osaka Organic Chemical Industry Ltd.) and 0.3% by mass of urea in pure water, which has the pH of 3.8 adjusted with sulfuric acid, followed by heating in an autoclave at 121° C. for 30 minutes. The molded body thus obtained was washed with a phosphate buffer solution while shaking at 250 rpm for 30 seconds. After replacing the phosphate buffer solution by a fresh phosphate buffer solution, the molded body was further heated in the autoclave at 121° C. for 30 minutes. The results obtained by evaluation of the molded body using the above method are shown in Tables 7 to 9.

Comparative Example 30

A commercially available hydrogel lens containing 2-hydroxyethyl methacrylate as a main component "Medalist (registered trademark) 1DAY PLUS" (manufactured by Bausch & Lomb Incorporated) was used as a substrate. The substrate was immersed in an aqueous solution containing 0.1% by mass of an acrylic acid/vinylpyrrolidone copolymer (molar ratio in copolymerization: 1/9, Mw: 400,000, manufactured by Osaka Organic Chemical Industry Ltd.) and 0.3% by mass of urea in pure water, which has the pH of 3.8 adjusted with sulfuric acid, followed by heating in an autoclave at 121° C. for 30 minutes. The molded body thus obtained was washed with a phosphate buffer solution while shaking at 250 rpm for 30 seconds. After replacing the phosphate buffer solution by a fresh phosphate buffer solution, the molded body was further heated in the autoclave at 121° C. for 30 minutes. The results obtained by evaluation of the molded body using the above method are shown in Tables 7 to 9.

Comparative Example 31

A commercially available silicone hydrogel lens containing polyvinylpyrrolidone and silicone as main components "1-Day Acuvue TruEye (registered trademark)" (manufactured by Johnson & Johnson) was used as a substrate. The substrate was immersed in an aqueous solution containing 0.2% by mass of an acrylic acid/N,N-dimethylacrylamide copolymer (molar ratio in copolymerization: 1/9, Mw: 800,000, manufactured by Osaka Organic Chemical Industry Ltd.) and 0.3% by mass of urea in pure water, which has the pH of 3.0 adjusted with sulfuric acid, followed by heating in an autoclave at 121° C. for 30 minutes. The molded body thus obtained was washed with a phosphate buffer solution while shaking at 250 rpm for 30 seconds. After replacing the phosphate buffer solution by a fresh phosphate buffer solution, the molded body was further heated in the autoclave at 121° C. for 30 minutes. The results obtained by evaluation of the molded body using the above method are shown in Tables 7 to 9.

Comparative Example 32

The results obtained by evaluation of a commercially available hydrogel lens containing 2-hydroxyethyl methacrylate as a main component "1-Day Acuvue (registered trademark)" (manufactured by Johnson & Johnson) using the above method are shown in Tables 7 to 9.

Comparative Example 33

The results obtained by evaluation of a commercially available silicone hydrogel lens containing polyvinylpyrrolidone and silicone as main components "1-Day Acuvue TruEye (registered trademark)" (manufactured by Johnson & Johnson) using the above method are shown in Tables 7 to 9.

Comparative Example 34

The results obtained by evaluation of a commercially available silicone hydrogel lens containing polyvinylpyrrolidone and silicone as main components "Acuvue Oasys (registered trademark)" (manufactured by Johnson & Johnson) using the above method are shown in Tables 7 to 9.

Comparative Example 35

The results obtained by evaluation of a commercially available silicone hydrogel lens, which has a surface subjected to a plasma treatment and contains silicone as a main component "AIR OPTIX EXAQUA (registered trademark)" (manufactured by Alcon Japan Ltd.), using the above method are shown in Tables 7 to 9.

Comparative Example 36

The results obtained by evaluation of a commercially available hydrogel lens containing 2-hydroxyethyl methacrylate obtained by copolymerizing an MPC monomer (2-methacryloyloxyethylphosphorylcholine) as a main component "Proclear 1 Day" (manufactured by Cooper Vision) using the above method are shown in Tables 7 to 9.

Comparative Example 37

The molded body obtained in Reference Example 1 was used as a substrate. The substrate was immersed in a solution containing 1.2% by mass of Polyacrylic acid "Sokalan (registered trademark) PA110S" (Mw: 250,000, manufactured by BASF) in pure water (pH 2.6) at 37° C. for 30 minutes. The molded body thus obtained was washed in pure water while shaking at 250 rpm for 10 seconds, followed by replacing by a fresh phosphate buffer solution. The results obtained by evaluation of the molded body using the above method are shown in Tables 7 to 9.

Comparative Example 38

A commercially available hydrogel lens containing 2-hydroxyethyl methacrylate as a main component "1-Day Acuvue (registered trademark)" (manufactured by Johnson & Johnson) was used as a substrate. The substrate was immersed in a solution containing 1.2% by mass of polyacrylic acid "Sokalan (registered trademark) PA110S" (Mw: 250,000, manufactured by BASF Japan) in pure water (pH 2.6) at 37° C. for 30 minutes. The molded body thus obtained was washed in pure water while shaking at 250 rpm for 10 seconds, followed by replacing by a fresh phosphate buffer solution. The results obtained by evaluation of the molded body using the above method are shown in Tables 7 to 9.

Comparative Example 39

A commercially available silicone hydrogel lens containing polyvinylpyrrolidone and silicone as main components "1-Day Acuvue TruEye (registered trademark)" (manufactured by Johnson & Johnson) was used as a substrate. The substrate was immersed in a solution containing 1.2% by mass of polyacrylic acid "Sokalan (registered trademark) PA110S" (Mw: 250,000, manufactured by BASF) in pure water (pH 2.6) at 37° C. for 30 minutes. The molded body thus obtained was washed in pure water while shaking at 250 rpm for 10 seconds, followed by replacing by a fresh phosphate buffer solution. The results obtained by evaluation of the molded body using the above method are shown in Tables 7 to 9.

Comparative Example 40

The molded body obtained in Reference Example 1 was used as a substrate. The substrate was immersed in an aqueous solution containing hydrochloric acid (pH 3.0) at room temperature for 5 minutes and then washed in pure water while shaking at 250 rpm for 10 seconds. Thereafter, the substrate was immersed in a solution containing 0.1% by mass of polyacrylic acid "Sokalan (registered trademark) PA110S" (Mw: 250,000, manufactured by BASF) in pure water (pH 3.3) at room temperature for 5 minutes. The molded body thus obtained was washed in pure water while shaking at 250 rpm for 10 seconds, followed by replacing by a fresh phosphate buffer solution. The results obtained by evaluation of the molded body using the above method are shown in Tables 7 to 9.

Comparative Example 41

A commercially available hydrogel lens containing 2-hydroxyethyl methacrylate as a main component "1-Day Acuvue (registered trademark)" (manufactured by Johnson & Johnson) was used as a substrate. The substrate was immersed in an aqueous solution containing hydrochloric acid (pH 3.0) at room temperature for 5 minutes and then washed in pure water while shaking at 250 rpm for 10 seconds. Thereafter, the substrate was immersed in a solution containing 0.1% by mass of polyacrylic acid "Sokalan (registered trademark) PA110S" (Mw: 250,000, manufactured by BASF) in pure water (pH 3.3) at room temperature for 5 minutes. The molded body thus obtained was washed in pure water while shaking at 250 rpm for 10 seconds, followed by replacing by a fresh phosphate buffer solution. The results obtained by evaluation of the molded body using the above method are shown in Tables 7 to 9.

Comparative Example 42

A commercially available silicone hydrogel lens containing polyvinylpyrrolidone and silicone as main components "1-Day Acuvue TruEye (registered trademark)" (manufactured by Johnson & Johnson) was used as a substrate. The substrate was immersed in an aqueous solution containing hydrochloric acid (pH 3.0) at room temperature for 5 minutes and then washed in pure water while shaking at 250 rpm for 10 seconds. Thereafter, the substrate was immersed in a solution containing 0.1% by mass of polyacrylic acid "Sokalan (registered trademark) PA110S" (Mw: 250,000, manufactured by BASF) in pure water (pH 3.3) at room temperature for 5 minutes. The molded body thus obtained was washed in pure water while shaking at 250 rpm for 10 seconds, followed by replacing by a fresh phosphate buffer solution. The results obtained by evaluation of the molded body using the above method are shown in Tables 7 to 9.

Comparative Example 43

The molded body obtained in Reference Example 1 was used as a substrate. After making a trial of immersing the substrate in a solution containing 0.1% by mass of chitosan (0.5% in 0.5% Acetic Acid at 20° C.) (manufactured by TCI Corporation) in pure water, a precipitate was formed in the solution due to inferior solubility of chitosan, thus failing to perform coating.

Comparative Example 44

The results obtained by evaluation of a commercially available hydrogel lens containing 2-hydroxyethyl methacrylate as a main component "Medalist (registered trademark) 1DAY PLUS" (manufactured by Bausch & Lomb Incorporated), using the above method are shown in Tables 7 to 9.

TABLE 7

| | Substrate | Moisture content of substrate (%) | Hydrophilic polymer and concentration of solution thereof | Initial pH | pH after heating treatment |
|---|---|---|---|---|---|
| Comparative Example 22 | "1-Day Acuvue Trueye" | 46 | 0.2% by mass Sodium alginate | 2.5 | 2.6 |
| Comparative Example 23 | "1-Day Acuvue" | 58 | 0.2% by mass Poloxamer 407 | 2.5 | 2.5 |
| Comparative Example 24 | "1-Day Acuvue Trueye" | 46 | 0.2% by mass Poloxamer 407 | 2.5 | 2.5 |
| Comparative Example 25 | "1-Day Acuvue" | 58 | 0.05% by mass Poly-2-acrylamido-2-methylpropanesulfonic acid | 6.8 | 6.9 |
| Comparative Example 26 | "1-Day Acuvue Trueye" | 46 | 0.05% by mass Poly-2-acrylamido-2-methylpropanesulfonic acid | 6.8 | 6.9 |
| Comparative Example 27 | "1-Day Acuvue" | 58 | 0.05% by mass 2-Acrylamido-2-methylpropanesulfonic acid/N,Ndimethylacrylamide copolymer | 6.8 | 6.9 |
| Comparative Example 28 | "1-Day Acuvue Trueye" | 46 | 0.05% by mass 2-Acrylamido-2-methylpropanesulfonic acid/N,Ndimethylacrylamide copolymer | 6.8 | 6.9 |
| Comparative Example 29 | Reference Example 1 | Less than 1% | 0.1% by mass Acrylic acid/vinylpyrrolidone copolymer Urea: 0.3% by mass | 3.8 | 7.0 |
| Comparative Example 30 | "Medalist 1 DAY PLUS" | 59 | 0.1% by mass Acrylic acid/vinylpyirolidone copolymer Urea: 0.3% by mass | 3.8 | 7.0 |
| Comparative Example 31 | "1-Day Acuvue Trueye" | 46 | 0.2% by mass Acrylic acid/N,N-dimethylacrylamide copolymer, Urea: 0.3% by mass | 3.0 | 7.0 |
| Comparative Example 32 | "1-Day Acuvue" | 58 | None | None | None |
| Comparative Example 33 | "1-Day Acuvue Trueye" | 46 | None | None | None |
| Comparative Example 34 | "Acuvue Oasys" | 38 | None | None | None |
| Comparative Example 35 | "AIR OPTIX EXAQUA" | 24 | None | None | None |
| Comparative Example 36 | "Proclear 1 Day" | 60 | None | None | None |
| Comparative Example 37 | Reference Example 1 | Less than 1% | 1.2% by mass Polyacrylic acid | None | None |
| Comparative Example 38 | "1-Day Acuvue" | 58 | 1.2% by mass Polyacrylic acid | None | None |

TABLE 7-continued

|  | Substrate | Moisture content of substrate (%) | Hydrophilic polymer and concentration of solution thereof | Initial pH | pH after heating treatment |
|---|---|---|---|---|---|
| Comparative Example 39 | "1-Day Acuvue Trueye" | 46 | 1.2% by mass Polyacrylic acid | None | None |
| Comparative Example 40 | Reference Example 1 | Less than 1% | 0.1% by mass Polyacrylic acid | None | None |
| Comparative Example 41 | "1-Day Acuvue" | 58 | 0.1% by mass Polyacrylic acid | None | None |
| Comparative Example 42 | "1-Day Acuvue Trueye" | 46 | 0.1% by mass Polyacrylic acid | None | None |
| Comparative Example 43 | Reference Example 1 | Less than 1% | 0.1% by mass chitosan | *Impossible to perform coating due to inferior solubility | *Impossible to perform coating due to inferior solubility |
| Comparative Example 44 | "Medalist 1 DAY PLUS" | 59 | None | None | None |

TABLE 8

|  | Liquid film retention time (seconds) | Lubricity | Moisture content of device (%) | Number of hydrophilic polymer layers | Moisture content change rate due to fixation of hydrophilic polymer layer (%) | Contact angle (°) | Friction coefficient |
|---|---|---|---|---|---|---|---|
| Comparative Example 22 | C (5 seconds) | C | 46 | Impossible to confirm layer | 0 | 46.0 | 0.110 |
| Comparative Example 23 | A (20 seconds) | D | 58 | Impossible to confirm layer | 0 | 52.1 | 0.445 |
| Comparative Example 24 | C (5 seconds) | C | 46 | Impossible to confirm layer | 0 | 46.8 | 0.105 |
| Comparative Example 25 | A (20 seconds) | D | 58 | Impossible to confirm layer | 0 | 52.0 | 0.450 |
| Comparative Example 26 | D (4 seconds) | C | 46 | Impossible to confirm layer | 0 | 46.5 | 0.109 |
| Comparative Example 27 | A (20 seconds) | D | 58 | Impossible to confirm layer | 0 | 52.1 | 0.450 |
| Comparative Example 28 | D (3 seconds) | C | 46 | Impossible to confirm layer | 0 | 46.1 | 0.105 |
| Comparative Example 29 | D (1 second) | E | Less than 1% | Impossible to confirm layer | 0 | 81.9 | 0.830 |
| Comparative Example 30 | B (15 seconds) | D | 59 | Impossible to confirm layer | 0 | 76.0 | 0.350 |
| Comparative Example 31 | D (2 seconds) | D | 46 | Impossible to confirm layer | 0 | 47.0 | 0.105 |
| Comparative Example 32 | A (20 seconds) | D | 58 | Impossible to confirm layer | None | 52.1 | 0.434 |
| Comparative Example 33 | D (3 seconds) | C | 46 | Impossible to confirm layer | None | 46.5 | 0.190 |
| Comparative Example 34 | A (20 seconds) | C | 38 | Impossible to confirm layer | None | 50.4 | 0.107 |
| Comparative Example 35 | D (4 seconds) | D | 24 | Impossible to confirm layer | None | 53.2 | 0.774 |
| Comparative Example 36 | D (4 seconds) | D | 60 | Impossible to confirm layer | None | 55.5 | 0.321 |
| Comparative Example 37 | E (0 second) | E | Less than 1% | Impossible to confirm layer | 0 | 75.0 | 0.834 |
| Comparative Example 38 | A (83 seconds) | D | 58 | Impossible to confirm layer | 0 | 45.1 | 0.201 |
| Comparative Example 39 | C (14 seconds) | C | 46 | Impossible to confirm layer | 0 | 40.0 | 0.100 |
| Comparative Example 40 | E (0 second) | E | Less than 1% | Impossible to confirm layer | 0 | 78.5 | 0.833 |
| Comparative Example 41 | A (70 seconds) | D | 58 | Impossible to confirm layer | 0 | 42.0 | 0.210 |
| Comparative Example 42 | B (17 seconds) | C | 46 | Impossible to confirm layer | 0 | 40.3 | 0.102 |

TABLE 8-continued

|  | Liquid film retention time (seconds) | Lubricity | Moisture content of device (%) | Number of hydrophilic polymer layers | Moisture content change rate due to fixation of hydrophilic polymer layer (%) | Contact angle (°) | Friction coefficient |
|---|---|---|---|---|---|---|---|
| Comparative Example 43 | *Impossible to perform coating due to inferior solubility | *Impossible to perform coating due to inferior solubility | *Impossible to perform coating due to inferior solubility | *Impossible to perform coating due to inferior solubility | *Impossible to perform coating due to inferior solubility | *Impossible to perform coating due to inferior solubility | *Impossible to perform coating due to inferior solubility |
| Comparative Example 44 | A (120 seconds) | D | 60 | Impossible to confirm layer | None | 74.6 | 0.380 |

TABLE 9

|  | Lipid deposition amount | Mucin deposition amount (μg/cm²) | Tensile elastic modulus of substrate (MPa) | Tensile elastic modulus of device (MPa) | Tensile elastic modulus change rate due to fixation of hydrophilic polymer layer (%) | Size of substrate (mm) | Size of device (mm) | Size change rate due to fixation of hydrophilic polymer layer (%) | Film thickness dried state of hydrophilic polymer layer (nm) | Film thickness frozen state of hydrophilic polymer layer (nm) |
|---|---|---|---|---|---|---|---|---|---|---|
| Comparative Example 22 | Deposited in area accounting for 1/5 of entire area | 1.01 | 0.70 | 0.71 | 0.40 | 14.20 | 14.20 | 0.0 | 0 | 0 |
| Comparative Example 23 | Not deposited | 2.30 | 0.30 | 0.29-4.4 | 14.20 | 14.10 | -0.7 | 0 | 0 | |
| Comparative Example 24 | Deposited in area accounting for 1/5 of entire area | 0.99 | 0.70 | 0.71 | 0.40 | 14.20 | 14.20 | 0.0 | 0 | 0 |
| Comparative Example 25 | Not deposited | 2.20 | 0.30 | 0.29 | -4.4 | 14.20 | 14.10 | -0.7 | 0 | 0 |
| Comparative Example 26 | Deposited in area accounting for 1/5 of entire area | 0.99 | 0.70 | 0.71 | 0.40 | 14.20 | 14.20 | 0.0 | 0 | 0 |
| Comparative Example 27 | Not deposited | 2.09 | 0.30 | 0.29 | -4.4 | 14.20 | 14.10 | -0.7 | 0 | 0 |
| Comparative Example 28 | Deposited in area accounting for 1/5 of entire area | 1.02 | 0.70 | 0.71 | 0.40 | 14.20 | 14.20 | 0.0 | 0 | 0 |
| Comparative Example 29 | Deposited on entire area | 3.09 | 0.53 | 0.49 | -6.8 | 14.00 | 14.00 | 0.0 | 0 | 0 |
| Comparative Example 30 | Not deposited | 2.60 | 0.26 | 0.27 | 5.1 | 14.00 | 14.00 | 0.0 | 0 | 0 |
| Comparative Example 31 | Deposited in area accounting for 1/5 of entire area | 1.04 | 0.70 | 0.71 | 0.40 | 14.20 | 14.10 | -0.7 | 0 | 0 |
| Comparative Example 32 | Not deposited | 2.10 | 0.30 | None | None | 14.20 | None | None | 0 | 0 |
| Comparative Example 33 | Deposited in area accounting for 1/5 of entire area | 0.94 | 0.70 | None | None | 14.20 | None | None | 0 | 0 |
| Comparative Example 34 | Not deposited | 1.18 | 0.70 | None | None | 14.00 | None | None | 0 | 0 |
| Comparative Example 35 | Not deposited | 2.59 | 1.47 | None | None | 13.80 | None | None | 0 | 0 |
| Comparative Example 36 | Not deposited | 5.07 | 0.39 | None | None | 14.20 | None | None | 0 | 0 |
| Comparative Example 37 | Deposited on entire area | 4.00 | 0.53 | 0.51 | -2.7 | 14.00 | 14.00 | 0.0 | 0 | 0 |
| Comparative Example 38 | Not deposited | 3.20 | 0.30 | 0.29 | -2.3 | 14.20 | 14.10 | -0.7 | 0 | 0 |
| Comparative Example 39 | Deposited in area accounting for 1/5 of entire area | 3.50 | 0.30 | 0.71 | 1.3 | 14.20 | 14.20 | 0.0 | 0 | 0 |
| Comparative Example 40 | Deposited on entire area | 3.89 | 0.53 | 0.53 | 1.3 | 14.00 | 14.00 | 0.0 | 0 | 0 |
| Comparative Example 41 | Not deposited | 2.99 | 0.30 | 0.29 | -4.2 | 14.20 | 14.10 | -0.7 | 0 | 0 |
| Comparative Example 42 | Deposited in area accounting for 1/5 of entire area | 3.90 | 0.70 | 0.73 | 3.3 | 14.20 | 14.15 | -0.4 | 0 | 0 |

TABLE 9-continued

| | Lipid deposition amount | Mucin deposition amount (μg/cm²) | Tensile elastic modulus of substrate (MPa) | Tensile elastic modulus of device (MPa) | Tensile elastic modulus change rate due to fixation of hydrophilic polymer layer (%) | Size of substrate (mm) | Size of device (mm) | Size change rate due to fixation of hydrophilic polymer layer (%) | Film thickness dried state of hydrophilic polymer layer (nm) | Film thickness frozen state of hydrophilic polymer layer (nm) |
|---|---|---|---|---|---|---|---|---|---|---|
| Comparative Example 43 | *Impossible to perform coating due to inferior solubility | *Impossible to perform coating due to inferior solubility | 0.53 | *Impossible to perform coating due to inferior solubility | *Impossible to perform coating due to inferior solubility | 14.00 | *Impossible to perform coating due to inferior solubility | *Impossible to perform coating due to inferior solubility | *Impossible to perform coating due to inferior solubility | *Impossible to perform coating due to inferior solubility |
| Comparative Example 44 | Not deposited | 2.47 | 0.26 | None | None | 14.20 | None | None | 0 | 0 |

The invention claimed is:

1. A device comprising:
a substrate; and
a hydrophilic polymer which is a copolymer of a monomer having a hydroxyl group and a monomer having an amide group, the hydrophilic polymer being separated into two or more layers,
wherein:
one of the hydrophilic polymer layers is fixed to at least a part of a surface of the substrate,
the monomer having a hydroxyl group is selected from the group consisting of methacrylic acid, acrylic acid, vinylbenzoic acid, thiophene-3-acetic acid, 4-styrenesulfonic acid, vinylsulfonic acid, 2-acrylamido-2-methylpropanesulfonic acid, and salts thereof;
the monomer having an amide group is selected from the group consisting of N-vinylpyrrolidone and N,N-dimethylacrylamide;
the device has a liquid film retention time of 20 seconds or more, and
lipid is not deposited on the device when the device is subjected to measurement of a lipid deposition amount according to the following method:
the device, 0.03 g of methyl palmitate as a lipid and 10 g of pure water were placed in a 20 cc screw tube, followed by shaking of the screw tube for 3 hours at 37° C. and 165 rpm, followed by scrubbing the device with tap water at 40° C. and a liquid detergent, after which the device is placed in a screw tube containing a phosphate buffer solution and stored at 4° C. for 1 hour before being visually observed, with the result that if a turbid portion existed, the methyl palmitate was judged to be deposited.

2. The device according to claim 1, wherein a contact angle of the device surface is 60° or less.

3. The device according to claim 1, wherein a friction coefficient of the device surface is 0.7 or less.

4. The device according to claim 1, which is a medical device.

5. The device according to claim 1, which is an ophthalmic lens, a dermal covering material, a wound dressing material, a skin protection material, a skin medicine carrier, an infusion tube, a gas delivery tube, a drain tube, a blood circuit, a covering tube, a catheter, a stent, a sheath, a tube connector, an access port, a biosensor chip, or an endoscopic dressing material.

6. The device according to claim 1, wherein one layer of the hydrophilic polymer is mixed with the substrate and the other layer is the hydrophilic polymer alone, the hydrophilic polymer layer mixed with the substrate being the layer fixed to at least a part of a surface of the substrate.

7. The device according to claim 1, wherein the monomer having a hydroxyl group is selected from the group consisting of acrylic acid and salts thereof.

* * * * *